United States Patent
Boyd et al.

(10) Patent No.: US 7,208,506 B2
(45) Date of Patent: Apr. 24, 2007

(54) HETEROARYLETHENYL DERIVATIVES, THEIR MANUFACTURE AND USE AS PHARMACEUTICAL AGENTS

(75) Inventors: Edward Boyd, Reading (GB); Frederick Brookfield, Benson (GB); Jonathan Gridley, Reading (GB); Manfred Kubbies, Penzberg (DE); Raymond Lau, Bracknell (GB); Ulrike Reiff, Penzberg (DE); Georg Tiefenthaler, Sindelsdorf (DE); Wolfgang von der Saal, Murnau (DE); Thomas von Hirschheydt, Penzberg (DE); Timothy Woodcock, Munich (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/477,641

(22) Filed: Jun. 29, 2006

(65) Prior Publication Data
US 2007/0010564 A1    Jan. 11, 2007

(30) Foreign Application Priority Data

| Jul. 7, 2005 | (EP) | ................... 05014789 |
| Jan. 18, 2006 | (EP) | ................... 06001008 |

(51) Int. Cl.
| A61K 31/38 | (2006.01) |
| A61K 31/42 | (2006.01) |
| A61K 31/425 | (2006.01) |
| A61K 31/44 | (2006.01) |

(52) U.S. Cl. .................. 514/347; 514/351; 514/357; 514/365; 514/378; 514/443; 514/438; 546/290; 548/204; 548/249; 549/58; 549/76

(58) Field of Classification Search ............... 514/347, 514/351, 357, 365, 378, 443, 438; 546/290; 548/204, 249; 549/58, 76
See application file for complete search history.

(56) References Cited

U.S. PATENT DOCUMENTS

| 4,206,142 A | 6/1980 | Matier et al. |
| 6,348,474 B1 | 2/2002 | Kayakiri et al. |
| 6,410,584 B1 | 6/2002 | Pamukcu et al. |
| 6,809,111 B2 * | 10/2004 | Carter .................. 514/378 |
| 6,911,469 B2 | 6/2005 | Kayakiri et al. |
| 2002/0099212 A1 | 7/2002 | Kayakiri et al. |
| 2004/0180947 A1 | 9/2004 | Kayakiri et al. |

FOREIGN PATENT DOCUMENTS

| WO | WO 99/00372 | 1/1999 |
| WO | WO 02/098848 | 12/2002 |
| WO | WO 03/035629 | 5/2003 |
| WO | WO 2004/048329 | 6/2004 |

OTHER PUBLICATIONS

Hirooka et al., Bull. Chem. Soc. Jap., 64, pp. 1431-1433 (1991).

* cited by examiner

*Primary Examiner*—Peter G. O'Sullivan
(74) *Attorney, Agent, or Firm*—George W. Johnston; Patricia S. Rocha-Tramaloni; Brian C. Remy

(57) ABSTRACT

The present invention relates to compounds of formula I formula I

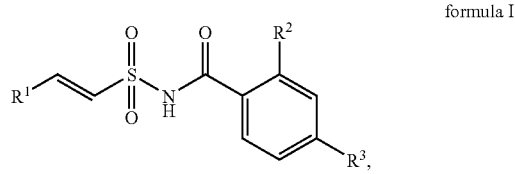

wherein $R^1$, $R^2$ and $R^3$ are defined herein, their pharmaceutically acceptable salts, enantiomeric forms, diastereoisomers and racemates, the preparation of the above compounds, medicaments containing them and their manufacture, as well as the use of the above compounds in the control or prevention of illnesses such as cancer.

48 Claims, No Drawings

HETEROARYLETHENYL DERIVATIVES, THEIR MANUFACTURE AND USE AS PHARMACEUTICAL AGENTS

PRIORITY TO RELATED APPLICATIONS

This application claims the benefit of European Application No. 05014789.1, filed Jul. 7, 2005 and European Application No. 06001008.9, filed Jan. 18, 2006, which are hereby incorporated by reference in their entirety.

The present invention relates to novel heteroarylethenyl derivatives, to a process for their manufacture, pharmaceutical compositions containing them and their manufacture as well as the use of these compounds as pharmaceutically active agents.

BACKGROUND OF THE INVENTION

The treatment of cancer diseases is of great importance in medicine. There is a worldwide need for effective cancer therapies in order to achieve a treatment which is appropriate to a patient and is target-orientated. This can be seen in the large number of scientific studies which have recently appeared in the fields of applied oncology and fundamental research relating to cancer therapy. The effects of tumor inhibitors are due to a very wide variety of mechanisms, only some of which are known. It is not unusual for known tumor drugs to be found to have new mechanisms of action. This is also to be expected in the case of the compounds according to the invention. Many tumor drugs act by way of mechanisms such as blockading the mechanism of cell division in the cell, preventing the tumor from being supplied with nutrients and oxygen (antiangiogenesis), preventing metastasis, preventing the reception and the onward transmission of growth signals to the tumor cell or forcing the tumor cell into programmed cell death (apoptosis).

Because they have different mechanisms of action, including interacting with different intracellular targets, the clinically relevant cytostatic agents are frequently administered in combination in order to achieve a synergistic therapeutic effect.

Hirooka, S., et al, Bull. Chem. Soc. Jap. 64 (1991) 1431–1433 relates to the synthesis of heteroarylethenyl sulfonamides like pyridyl- or thienyl-ethenylsulfonamide. Some styrylsulfonamide derivatives are known as inhibitors of neoplastic cells from U.S. Pat. No. 6,410,584 B1. WO 99/00372 relates to styrylsulfonamide derivatives as hypoglycemics and U.S. Pat. No. 4,206,142 describes styrylsulfonamides as intermediates of analgetic styrylsulfonylamidines.

WO 2003/035629 relates to thiophene- and thiazolesulfonamides as antineoplastic agents. WO 02/098848 and WO 2004/048329 relate to benzoylsulfonamides as antitumor agents.

SUMMARY OF THE INVENTION

The present invention relates to heteroarylethenyl derivatives of the general formula I

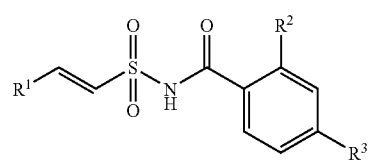

formula I wherein
R$^1$, R$^2$ and R$^3$ are as described herein and the pharmaceutically acceptable salts thereof.

The compounds according to this invention show antiproliferative activity and inhibit the growth of tumor cells in vitro and in vivo. Objects of the present invention are the compounds of formula I and their tautomers, pharmaceutically acceptable salts, enantiomeric forms, diastereoisomers and racemates, their use for the inhibition of tumor growth, the preparation of the above-mentioned compounds, medicaments containing them and their manufacture as well as the use of the above-mentioned compounds in the control or prevention of illnesses, especially of cancers such as colorectal, breast, lung, prostate, pancreatic, gastric, bladder, ovarian, melanoma, neuroblastoma, cervical, kidney or renal cancers, leukemias or lymphomas, or in the manufacture of corresponding medicaments.

DETAILED DESCRIPTION OF THE INVENTION

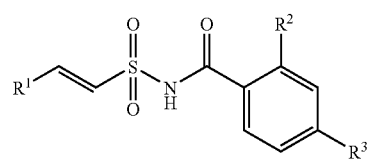

formula I wherein
R$^1$ is a mono- or bicyclic heteroaryl which is optionally substituted one to three times by alkyl, or one or two times by halogen, cyano, alkoxy, halogenated alkyl, halogenated alkoxy or amino;
R$^2$ is chlorine, bromine, methyl, trifluoromethyl or methoxy;
R$^3$ is chlorine, bromine, fluorine, methyl or trifluoromethyl;

and the pharmaceutically acceptable salts thereof.

One embodiment of the invention are the compounds of formula I, wherein
R$^1$ is a monocyclic heteroaryl which is optionally substituted one to three times by alkyl, or one or two times by halogen, cyano, alkoxy, halogenated alkyl, halogenated alkoxy or amino; and
R$^2$ and R$^3$ are chlorine.

The term "monocyclic heteroaryl" means a monocyclic aromatic ring with 5 to 6 ring atoms, which contains up to 3, preferably 1 or 2 heteroatoms selected independently from N, O or S and the remaining ring atoms being carbon atoms. Such heteroaryl groups can be optionally substituted one to three, preferably one or two times by a) alkyl, and/or the heteroaryl group can be optionally substituted one or two, preferably one time by b) halogen, c) cyano, d) alkoxy, e)

halogenated alkyl f) halogenated alkoxy, or g) amino. Preferably the monocyclic heteroaryl group can be optionally substituted by a) alkyl, b) halogen, c) alkoxy, d) halogenated alkyl, e) halogenated alkoxy and more preferred by a) alkyl, b) halogen, c) alkoxy, or d) halogenated alkyl, and still more preferred by a) alkyl, or d) alkoxy. Examples of such monocyclic heteroaryl groups are thienyl such as thiophen-2-yl, thiophen-3-yl, 5-methyl-thiophen-2-yl, 4-methyl-thiophen-2-yl, 3-methyl-thiophen-2-yl, 4,5-dimethyl-thiophen-2-yl, 3-bromo-thiophen-2-yl, 4-bromo-thiophen-2-yl, 4-bromo-thiophen-3-yl, pyridyl such as pyridin-4-yl, pyridin-3-yl, pyridin-2-yl, 3-fluoro-pyridin-4-yl, 6-methyl-pyridin-2-yl, 6-methoxy-pyridin-3-yl, 6-chloro-pyridin-3-yl, 2-chloro-pyridin-3-yl, 6-trifluoromethyl-pyridin-3-yl, 5-trifluoromethoxy-pyridin-2-yl, furyl, pyrrolyl, pyrazolyl, dimethylisoxazolyl, imidazolyl, oxazolyl, isoxazolyl, thiazolyl, isothiazolyl, pyrimidyl, pyrazinyl, pyridazinyl, triazinyl, thiadiazolyl, oxadiazolyl, triazolyl, and the like, preferably thienyl, pyridyl, imidazolyl, pyrazolyl, [1,2,3]triazolyl, thiazolyl, furyl, pyrimidyl, pyrazinyl, pyridazinyl or [1,3,5]triazinyl and more preferred thiophen-2-yl, thiophen-3-yl, 4-bromo-thiophen-3-yl, 3-chloro-thiophen-2-yl, pyridin-4-yl, pyridin-3-yl, pyridin-2-yl, 6-methyl-pyridin-2-yl, 6-methoxy-pyridin-3-yl, 6-trifluoromethyl-pyridin-3-yl, 5-trifluoromethoxy-pyridin-2-yl, 1-methyl-1H-imidazol-4-yl, 1-methyl-1H-imidazol-2-yl, 2-methyl-2H-pyrazol-3-yl, 3-methyl-3H-[1,2,3]triazol-4-yl, 5-methyl-furan-2-yl, thiazole-2-yl, pyrimidin-5-yl, pyrazine-2-yl, pyridazine-3-yl, pyridazine-4-yl, [1,3,5]triazin-2-yl.

Preferably the monocyclic heteroaryl is selected from the group consisting of thienyl, pyridyl, isoxazolyl, pyrimidyl and thiazolyl all optionally substituted by a) alkyl, b) halogen, c) alkoxy, or d) halogenated alkyl. Examples of such preferred monocyclic heteroaryl include thiophen-2-yl, thiophen-3-yl, 5-methyl-thiophen-2-yl, 3-methyl-thiophen-2-yl, 4-methyl-thiophen-2-yl, 4-bromo-thiophen-2-yl, 3-bromo-thiophen-2-yl, pyridin-2-yl, pyridin-3-yl, pyridin-4-yl, 6-methoxy-pyridin-3-yl, 6-methyl-pyridin-2-yl, 6-trifluoromethyl-pyridin-3-yl, 6-chloro-pyridin-3-yl, 2-chloro-pyridin-3-yl, 3,5-dimethyl-isoxazol-4-yl, pyrimidin-5-yl and thiazol-2-yl.

The term "bicyclic heteroaryl" means a bicyclic aromatic ring with 9 to 10 ring atoms, preferably 9 ring atoms, which contains up to 3, preferably 1 or 2 heteroatoms selected independently from N, O or S and the remaining ring atoms being carbon atoms. Such heteroaryl groups can be optionally substituted one to three, preferably one or two times by a) alkyl, and/or the heteroaryl group can be optionally substituted one or two, preferably one time by b) halogen, c) cyano, d) alkoxy, e) halogenated alkyl f) halogenated alkoxy, or g) amino. Preferably the bicyclic heteroaryl group is unsubstituted Examples of such bicyclic heteroaryl groups include benzothiophenyl, indolyl, benzofuranyl, benzimidazolyl, benzothiazolyl, benzoxazolyl, quinolinyl, isoquinolinyl, quinazolinyl and the like, preferably benzothiophenyl, indolyl, benzimidazolyl, benzothiazolyl and more preferably benzothiophenyl such as benzo[b]thiophen-3-yl.

Preferably the mono- or bicyclic heteroaryl is selected from the group consisting of thienyl, pyridyl, isoxazolyl, pyrimidyl, thiazolyl and benzothiophenyl all optionally substituted by a) alkyl, b) halogen, c) alkoxy, or d) halogenated alkyl. In such group, preferably the bicyclic heteroaryl is unsubstituted while the monocyclic heteroaryl can be optionally substituted by a) alkyl, b) halogen, c) alkoxy, or d) halogenated alkyl. Examples of such preferred mono- or bicyclic heteroaryl include thiophen-2-yl, thiophen-3-yl, 5-methyl-thiophen-2-yl, 3-methyl-thiophen-2-yl, 4-methyl-thiophen-2-yl, 4-bromo-thiophen-2-yl, 3-bromo-thiophen-2-yl, pyridin-2-yl, pyridin-3-yl, pyridin-4-yl, 6-methoxy-pyridin-3-yl, 6-methyl-pyridin-2-yl, 6-trifluoromethyl-pyridin-3-yl, 6-chloro-pyridin-3-yl, 2-chloro-pyridin-3-yl, 3,5-dimethyl-isoxazol-4-yl, pyrimidin-5-yl, thiazol-2-yl and benzo[b]thiophen-3-yl.

Preferably the heteroaryl in the definition of $R^1$ is monocyclic.

An embodiment of the invention are the compounds of formula I, wherein the heteroaryl in the definition of $R^1$ is a monocyclic aromatic ring with 5 to 6 ring atoms, which contains 1 heteroatom selected independently from N, O or S and the remaining ring atoms being carbon atoms.

Examples of such monocyclic heteroaryl groups containing 1 heteroatom are e.g. thienyl, pyridyl, furyl or pyrrolyl, preferably thienyl, pyridyl or furyl, more preferably thienyl or pyridyl.

An embodiment of the invention are the compounds of formula I, wherein the heteroaryl in the definition of $R^1$ is a monocyclic aromatic ring with 5 to 6 ring atoms, which contains 2 heteroatoms selected independently from N, O or S and the remaining ring atoms being carbon atoms.

Examples of such monocyclic heteroaryl groups containing 2 heteroatoms are e.g. pyrazolyl, imidazolyl, oxazolyl, isoxazolyl, thiazolyl, isothiazolyl, pyrimidyl, pyrazinyl, pyridazinyl, preferably pyrazolyl, imidazolyl, isoxazolyl, thiazolyl, pyrimidyl, pyrazinyl or pyridazinyl and more preferably isoxazolyl, pyrimidyl or thiazolyl and still more preferably isoxazolyl.

An embodiment of the invention are the compounds of formula I, wherein the heteroaryl in the definition of $R^1$ is a monocyclic aromatic ring with 5 to 6 ring atoms, which contains 3 heteroatoms selected independently from N, O or S and the remaining ring atoms being carbon atoms.

Examples of such monocyclic heteroaryl groups containing 3 heteroatoms are e.g. triazinyl, thiadiazolyl, oxadiazolyl, triazolyl, preferably triazinyl or triazolyl, and more preferably triazolyl.

An embodiment of the invention are the compounds of formula I, wherein the heteroaryl in the definition of $R^1$ is a bicyclic aromatic ring with 9 to 10 ring atoms, preferably 9 ring atoms, which contains 1 heteroatom selected independently from N, O or S and the remaining ring atoms being carbon atoms.

Examples of such bicyclic heteroaryl groups containing 1 heteroatom are e.g. benzothiophenyl, indolyl or benzofuranyl, preferably benzothiophenyl or indolyl and more preferably benzothiophenyl.

The term "alkyl" as used herein means a saturated, straight-chain or branched-chain hydrocarbon containing from 1 to 6, preferably 1 to 4, and more preferred 1 to 3, carbon atoms, such as methyl, ethyl, n-propyl, isopropyl, n-butyl, 2-butyl, t-butyl, n-pentyl, 3-methyl-butyl, 2-methyl-butyl, n-hexyl, 3-methyl-pentyl, 2-ethyl-butyl, 3,3-dimethyl-butyl, 2,2-dimethyl-butyl or 2,3-dimethyl-butyl.

The term "halogen" as used herein means fluorine, chlorine, bromine or iodine, preferably fluorine, chlorine or bromine and especially chlorine or bromine.

The term "alkoxy" as used herein means an alkyl group as defined above which is attached via an oxygen (—O—).

The term "halogenated alkyl" as used herein means an alkyl group as defined above which is substituted one or several times by halogen, preferably by fluorine or chlorine, especially by fluorine. Examples are difluoromethyl, trifluoromethyl, 2,2,2-trifluoroethyl, perfluorethyl, and the like, preferably trifluoromethyl.

The term "halogenated alkoxy" as used herein means an alkoxy group as defined above which is substituted one or several times by halogen, preferably by fluorine or chlorine, especially by fluorine. Examples are difluoromethoxy, trifluoromethoxy, 2,2,2-trifluoroethoxy, perfluoroethoxy and the like, preferably trifluoromethoxy and difluoromethoxy and preferably trifluoromethoxy.

As used herein, in relation to mass spectrometry (MS) the term "API+" refers to positive atmospheric pressure ionization mode, the term "API–" refers to negative atmospheric pressure ionization mode, the term "ESI+" refers to positive electrospray ionization mode and the term "M+H" refers to protonated molecular ions.

In relation to the processes described herein for the preparation of the compounds of the present invention, the term "activated before" means that the carboxylic acid group is converted into a reactive carboxylic acid derivative before the reaction. Such activation is typically carried out either without solvent, or in solvents like dichloromethane, dichloroethane, tetrahydrofuran, dioxane and mixtures thereof, at temperatures between 0° C. and 100° C. Typical methods used for the activation are chlorination or formation of an imidazolide. Typically used chlorinating reagents are thionylchloride, oxalyl chloride, phosphorus trichloride, phosphorus pentachloride, phosphorus oxychloride, N-chlorosuccinamide triphenylphosphine. A typically used imidazolination method is the reaction with N,N'-carbonyl diimidazole (CDI). Other typically used activation methods include the use of activating agents such as 1-ethyl-3-(3'-dimethylaminopropyl)carbodiimide (EDCI), hydroxy-benzotriazole (HOBt) and the like.

An embodiment of the invention are the compounds of formula I, wherein
$R^1$ is a monocyclic heteroaryl which is optionally substituted one to three times by alkyl, or one or two times by halogen, alkoxy, halogenated alkyl or halogenated alkoxy.

Another embodiment of the invention are the compounds of formula I, wherein
$R^1$ is a monocyclic heteroaryl which is optionally substituted one or two times by alkyl, halogen, alkoxy or halogenated alkyl.

Another embodiment of the invention are the compounds of formula I, wherein
$R^1$ is a mono- or bicyclic heteroaryl which is optionally substituted one to three times by alkyl, or one or two times by halogen, alkoxy or halogenated alkyl.

Another embodiment of the invention are the compounds of formula I, wherein
$R^1$ is a thienyl or pyridyl which is optionally substituted one or two times by alkyl, halogen, alkoxy, halogenated alkyl or halogenated alkoxy;

Another embodiment of the invention are the compounds of formula I, wherein
$R^1$ is a thienyl or pyridyl which is optionally substituted one or two times by alkyl, halogen, alkoxy or halogenated alkyl.

Another embodiment of the invention are the compounds of formula I, wherein
$R^1$ is thienyl or pyridyl which is optionally substituted one or two times by alkyl or alkoxy.

Another embodiment of the invention are the compounds of formula I, wherein
$R^1$ is thienyl, isoxazolyl or pyridyl which is optionally substituted one or two times by alkyl or alkoxy.

Another embodiment of the invention are the compounds of formula I, wherein
$R^1$ is thienyl.

Another embodiment of the invention are the compounds of formula I, wherein
$R^1$ is thienyl; and
$R^2$ and $R^3$ are chlorine.

Such compounds, for example, may be selected from the group consisting of:
(E)-2-Thiophen-2-yl-ethenesulfonic acid 2,4-dichloro-benzoylamide; and
(E)-2-Thiophen-3-yl-ethenesulfonic acid 2,4-dichloro-benzoylamide.

Another embodiment of the invention are the compounds of formula I, wherein
$R^1$ is thienyl or isoxazolyl which is optionally substituted one or two times by alkyl; and
$R^2$ and $R^3$ are chlorine.

Such compounds, for example, may be selected from the group consisting of:
(E)-2-(3-Methyl-thiophen-2-yl)-ethenesulfonic acid 2,4-dichloro-benzoylamide;
(E)-2-(5-Methyl-thiophen-2-yl)-ethenesulfonic acid 2,4-dichloro-benzoylamide;
(E)-2-(4-Methyl-thiophen-2-yl)-ethenesulfonic acid 2,4-dichloro-benzoylamide; and
(E)-2-(3,5-Dimethyl-isoxazol-4-yl)-ethenesulfonic acid 2,4-dichloro-benzoylamide; sodium salt.

Another embodiment of the invention are the compounds of formula I, wherein
$R^1$ is pyridyl which is optionally substituted one or two times by alkyl or alkoxy.

Another embodiment of the invention are the compounds of formula I, wherein
$R^1$ is pyridyl which is optionally substituted one or two times by alkyl or alkoxy; and
$R^2$ and $R^3$ are chlorine.

Such compounds, for example, may be selected from the group consisting of:
(E)-2-Pyridin-2-yl-ethenesulfonic acid 2,4-dichloro-benzoylamide; sodium salt;
(E)-2-Pyridin-3-yl-ethenesulfonic acid 2,4-dichloro-benzoylamide; sodium salt;
(E)-2-Pyridin-4-yl-ethenesulfonic acid 2,4-dichloro-benzoylamide; sodium salt;
(E)-2-(6-Methoxy-pyridin-3-yl)-ethenesulfonic acid 2,4-dichloro-benzoylamide; sodium salt; and
(E)-2-(6-Methyl-pyridin-2-yl-ethenesulfonic acid 2,4-dichloro-benzoylamide; sodium salt.

Another embodiment of the invention are the compounds of formula I, wherein
$R^1$ is thienyl or pyridyl which is optionally substituted one or two times by halogen or halogenated alkyl.; and
$R^2$ and $R^3$ are chlorine.

Such compounds, for example, may be selected from the group consisting of:
(E)-2-(4-Bromo-thiophen-2-yl)-ethenesulfonic acid 2,4-dichloro-benzoylamide; sodium salt;
(E)-2-(3-Bromo-thiophen-2-yl)-ethenesulfonic acid 2,4-dichloro-benzoylamide; sodium salt;
(E)-2-(6-Trifluoromethyl-pyridin-3-yl)-ethenesulfonic acid 2,4-dichloro-benzoylamide; sodium salt;
(E)-2-(6-Chloro-pyridin-3-yl)-ethenesulfonic acid 2,4-dichloro-benzoylamide; sodium salt; and
(E)-2-(2-Chloro-pyridin-3-yl)-ethenesulfonic acid 2,4-dichloro-benzoylamide; sodium salt.

Another embodiment of the invention are the compounds of formula I, wherein $R^1$ is pyrimidyl or thiazolyl; and
$R^2$ and $R^3$ are chlorine.
Such compounds, for example, may be selected from the group consisting of:
(E)-2-Pyrimidin-5-yl-ethenesulfonic acid 2,4-dichloro-benzoylamide; sodium salt; and
(E)-2-Thiazol-2-yl-ethenesulfonic acid 2,4-dichloro-benzoylamide; sodium salt.
Another embodiment of the invention are the compounds of formula I, wherein
$R^1$ is benzothiophenyl; and
$R^2$ and $R^3$ are chlorine.
Such compounds, for example, may be selected from the group consisting of:
(E)-2-Benzo[b]thiophen-3-yl-ethenesulfonic acid 2-chloro-4-fluoro-benzoylamide; sodium salt;
(E)-2-Benzo[b]thiophen-3-yl-ethenesulfonic acid 2,4-dichloro-benzoylamide; sodium salt;
(E)-2-Benzo[b]thiophen-3-yl-ethenesulfonic acid 4-fluoro-2-trifluoromethyl-benzoylamide; sodium salt;
(E)-2-Benzo[b]thiophen-3-yl-ethenesulfonic acid 2,4-ditrifluoromethyl-benzoylamide; sodium salt;
(E)-2-Benzo[b]thiophen-3-yl-ethenesulfonic acid 4-chloro-2-methyl-benzoylamide; sodium salt; and
(E)-2-Benzo[b]thiophen-3-yl-ethenesulfonic acid 2-bromo-4-fluoro-benzoylamide; sodium salt.
Another embodiment of the invention are the compounds of formula I, wherein
$R^2$ is chlorine; and
$R^3$ is bromine.
Such compounds, for example, may be selected from the group consisting of:
(E)-2-Pyridin-2-yl-ethenesulfonic acid 4-bromo-2-chloro-benzoylamide; sodium salt;
(E)-2-Pyridin-3-yl-ethenesulfonic acid 4-bromo-2-chloro-benzoylamide; sodium salt;
(E)-2-Thiophen-3-yl-ethenesulfonic acid 4-bromo-2-chloro-benzoylamide; sodium salt;
(E)-2-Thiophen-2-yl-ethenesulfonic acid 4-bromo-2-chloro-benzoylamide; sodium salt;
Another embodiment of the invention are the compounds of formula I, wherein
$R^2$ is chlorine; and
$R^3$ is fluorine.
Such compounds, for example, may be selected from the group consisting of:
(E)-2-Pyridin-2-yl-ethenesulfonic acid 2-chloro-4-fluoro-benzoylamide; sodium salt;
(E)-2-Pyridin-3-yl-ethenesulfonic acid 2-chloro-4-fluoro-benzoylamide; sodium salt;
(E)-2-(6-Methoxy-pyridin-3-yl)-ethenesulfonic acid 2-chloro-4-fluoro-benzoylamide; sodium salt;
(E)-2-Thiophen-3-yl-ethenesulfonic acid 2-chloro-4-fluoro-benzoylamide; sodium salt;
(E)-2-Thiophen-2-yl-ethenesulfonic acid 2-chloro-4-fluoro-benzoylamide; sodium salt; and
(E)-2-(6-Methyl-pyridin-2-yl)-ethenesulfonic acid 2-chloro-4-fluoro-benzoylamide; sodium salt.
Another embodiment of the invention are the compounds of formula I, wherein
$R^2$ is bromine; and
$R^3$ is chlorine.
Another embodiment of the invention are the compounds of formula I, wherein
$R^2$ is bromine; and
$R^3$ is fluorine.
Such compounds, for example, may be selected from the group consisting of:
(E)-2-Pyridin-2-yl-ethenesulfonic acid 2-bromo-4-fluoro-benzoylamide; sodium salt;
(E)-2-(6-Methoxy-pyridin-3-yl)-ethenesulfonic acid 2-bromo-4-fluoro-benzoylamide; sodium salt;
(E)-2-(6-Methyl-pyridin-2-yl)-ethenesulfonic acid 2-bromo-4-fluoro-benzoylamide; sodium salt;
(E)-2-Thiophen-3-yl-ethenesulfonic acid 2-bromo-4-fluoro-benzoylamide; sodium salt; and
(E)-2-Thiophen-2-yl-ethenesulfonic acid 2-bromo-4-fluoro-benzoylamide; sodium salt.
Another embodiment of the invention are the compounds of formula I, wherein
$R^2$ is bromine; and
$R^3$ is methyl.
Such compounds, for example, may be selected from the group consisting of:
(E)-2-Pyridin-2-yl-ethenesulfonic acid 2-bromo-4-methyl-benzoylamide; sodium salt;
(E)-2-Pyridin-3-yl-ethenesulfonic acid 2-bromo-4-methyl-benzoylamide; sodium salt;
(E)-2-Thiophen-3-yl-ethenesulfonic acid 2-bromo-4-methyl-benzoylamide; sodium salt; and
(E)-2-Thiophen-2-yl-ethenesulfonic acid 2-bromo-4-methyl-benzoylamide; sodium salt.
Another embodiment of the invention are the compounds of formula I, wherein
$R^2$ is methyl; and
$R^3$ is chlorine.
Such compounds, for example, may be selected from the group consisting of:
(E)-2-Pyridin-2-yl-ethenesulfonic acid 4-chloro-2-methyl-benzoylamide; sodium salt;
(E)-2-Pyridin-3-yl-ethenesulfonic acid 4-chloro-2-methyl-benzoylamide; sodium salt;
(E)-2-(6-Methoxy-pyridin-3-yl)-ethenesulfonic acid 4-chloro-2-methyl-benzoylamide; sodium salt;
(E)-2-(6-Methyl-pyridin-2-yl)-ethenesulfonic acid 4-chloro-2-methyl-benzoylamide; sodium salt;
(E)-2-Thiophen-3-yl-ethenesulfonic acid 4-chloro-2-methyl-benzoylamide; sodium salt; and
(E)-2-Thiophen-2-yl-ethenesulfonic acid 4-chloro-2-methyl-benzoylamide; sodium salt.
Another embodiment of the invention are the compounds of formula I, wherein
$R^2$ is methyl; and
$R^3$ is bromine.
Such compounds, for example, may be selected from the group consisting of:
(E)-2-Pyridin-2-yl-ethenesulfonic acid 4-bromo-2-methyl-benzoylamide; sodium salt;
(E)-2-Pyridin-3-yl-ethenesulfonic acid 4-bromo-2-methyl-benzoylamide; sodium salt;
(E)-2-Thiophen-3-yl-ethenesulfonic acid 4-bromo-2-methyl-benzoylamide; sodium salt; and
(E)-2-Thiophen-2-yl-ethenesulfonic acid 4-bromo-2-methyl-benzoylamide; sodium salt.
Another embodiment of the invention are the compounds of formula I, wherein
$R^2$ is methyl; and
$R^3$ is fluorine.
Such a compound, for example, may be selected from:
(E)-2-Thiophen-2-yl-ethenesulfonic acid 4-fluoro-2-methyl-benzoylamide.
Another embodiment of the invention are the compounds of formula I, wherein $R^2$ is methyl; and
$R^3$ is methyl.

Such compounds, for example, may be selected from the group consisting of:
(E)-2-Thiophen-2-yl-ethenesulfonic acid 2,4-dimethyl-benzoylamide; sodium salt;
(E)-2-Pyridin-3-yl-ethenesulfonic acid 2,4-dimethyl-benzoylamide; sodium salt;
(E)-2-Thiophen-3-yl-ethenesulfonic acid 2,4-dimethyl-benzoylamide; sodium salt; and
(E)-2-Pyridin-4-yl-ethenesulfonic acid 2,4-dimethyl-benzoylamide; sodium salt.

Another embodiment of the invention are the compounds of formula I, wherein
$R^2$ is trifluoromethyl; and
$R^3$ is chlorine.

Another embodiment of the invention are the compounds of formula I, wherein
$R^2$ is trifluoromethyl; and
$R^3$ is fluorine.

Such compounds, for example, may be selected from the group consisting of:
(E)-2-Pyridin-2-yl-ethenesulfonic acid 4-fluoro-2-trifluoromethyl-benzoylamide; sodium salt;
(E)-2-Pyridin-3-yl-ethenesulfonic acid 4-fluoro-2-trifluoromethyl-benzoylamide; sodium salt;
(E)-2-(6-Methoxy-pyridin-3-yl)-ethenesulfonic acid 4-fluoro-2-trifluoromethyl-benzoylamide; sodium salt;
(E)-2-(6-Methyl-pyridin-2-yl)-ethenesulfonic acid 4-fluoro-2-trifluoromethyl-benzoylamide; sodium salt; and
(E)-2-Thiophen-3-yl-ethenesulfonic acid 4-fluoro-2-trifluoromethyl-benzoylamide; sodium salt.

Another embodiment of the invention are the compounds of formula I, wherein
$R^2$ is trifluoromethyl; and
$R^3$ is methyl.

Another embodiment of the invention are the compounds of formula I, wherein
$R^2$ is trifluoromethyl; and
$R^3$ is trifluoromethyl.

Such compounds, for example, may be selected from the group consisting of:
(E)-2-Pyridin-2-yl-ethenesulfonic acid 2,4-bis-trifluoromethyl-benzoylamide; sodium salt;
(E)-2-Pyridin-3-yl-ethenesulfonic acid 2,4-bis-trifluoromethyl-benzoylamide; sodium salt;
(E)-2-(6-Methoxy-pyridin-3-yl)-ethenesulfonic acid 2,4-bis-trifluoromethyl-benzoylamide; sodium salt;
(E)-2-(6-Methyl-pyridin-2-yl)-ethenesulfonic acid 2,4-bis-trifluoromethyl-benzoylamide; sodium salt;
(E)-2-Thiophen-3-yl-ethenesulfonic acid 2,4-bis-trifluoromethyl-benzoylamide; sodium salt;
(E)-2-Thiophen-2-yl-ethenesulfonic acid 2,4-bis-trifluoromethyl-benzoylamide; sodium salt; and
(E)-2-Pyridin-3-yl-ethenesulfonic acid 2,4-bis-trifluoromethyl-benzoylamide.

Another embodiment of the invention are the compounds of formula I, wherein
$R^2$ is methoxy; and
$R^3$ is chlorine.

Such compounds, for example, may be selected from the group consisting of:
(E)-2-Pyridin-3-yl-ethenesulfonic acid 4-chloro-2-methoxy-benzoylamide; sodium salt;
(E)-2-Pyridin-2-yl-ethenesulfonic acid 4-chloro-2-methoxy-benzoylamide; sodium salt;
(E)-2-Thiophen-2-yl-ethenesulfonic acid 4-chloro-2-methoxy-benzoylamide; sodium salt; and
(E)-2-Thiophen-3-yl-ethenesulfonic acid 4-chloro-2-methoxy-benzoylamide; sodium salt.

Another embodiment of the invention are the compounds of formula I, wherein
$R^2$ is methoxy; and
$R^3$ is bromine.

Another embodiment of the invention are the compounds of formula I, wherein
$R^2$ is methoxy; and
$R^3$ is fluorine.

Another embodiment of the invention are the compounds of formula I, wherein
$R^2$ is methoxy; and
$R^3$ is trifluoromethyl.

Another embodiment of the invention are the compounds of formula I, wherein
$R^3$ is fluorine.

Another embodiment of the invention are the compounds of formula I, wherein
$R^1$ is thienyl or pyridyl which is optionally substituted one or two times by alkyl, halogen, alkoxy or halogenated alkyl; and
$R^3$ is fluorine.

Another embodiment of the invention are the compounds of formula I, wherein
$R^1$ is thienyl such as thiophen-2-yl or thiophen-3-yl;
$R^2$ is chlorine, bromine or trifluoromethyl; and
$R^3$ is fluorine.

Another embodiment of the invention are the compounds of formula I, wherein
$R^1$ is pyridyl which is optionally substituted one or two times by alkyl, halogen, alkoxy or halogenated alkyl;
$R^2$ is chlorine, bromine or trifluoromethyl; and
$R^3$ is fluorine.

Another embodiment of the invention are the compounds of formula I, wherein
$R^3$ is chlorine.

Another embodiment of the invention are the compounds of formula I, wherein
$R^1$ is thienyl or pyridyl which is optionally substituted one or two times by alkyl, halogen, alkoxy or halogenated alkyl; and
$R^3$ is chlorine.

Another embodiment of the invention are the compounds of formula I, wherein
$R^1$ is thienyl such as thiophen-2-yl or thiophen-3-yl;
$R^2$ is methyl or methoxy; and
$R^3$ is chlorine.

Another embodiment of the invention are the compounds of formula I, wherein
$R^1$ is pyridyl which is optionally substituted one or two times by alkyl, halogen, alkoxy or halogenated alkyl;
$R^2$ is methyl or methoxy; and
$R^3$ is chlorine.

Another embodiment of the invention is a process for the preparation of the compounds of formula I, comprising the steps of
a) reacting a compound of formula II

formula II wherein R¹ has the significance given for formula I and X is iodine or bromine, with ethenesulfonic acid (1,1,3,3-tetramethyl-butyl)-amide,

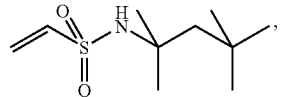

to give the compounds of formula III,

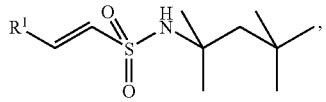

formula III wherein R¹ has the significance given for formula I, b) cleaving the 1,1,3,3-tetramethyl-butyl group of the compounds of formula III to give the free sulfonamides of formula IV,

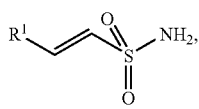

formula IV wherein R¹ has the significance given for formula I, and c) reacting the sulfonamides of formula IV with the benzoic acid of formula IX,

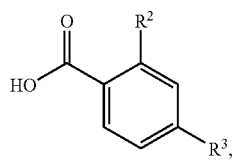

formula IX which is activated before, and wherein R² and R³ have the significance given for formula I, to give the compounds of formula I,

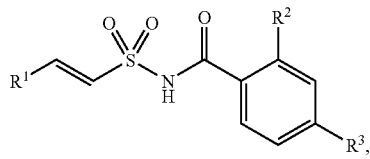

formula I wherein R¹, R² and R³ have the significance given for formula I.

Another embodiment of the invention is a process for the preparation of the compounds of formula I, comprising the steps of a) reacting a compound of formula V

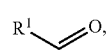

formula V wherein R¹ has the significance given for formula I, with N-(1,1,3,3-tetramethyl-butyl)-methanesulfonamide,

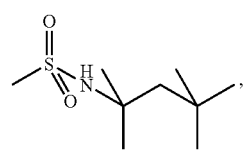

to give the compounds of formula VI,

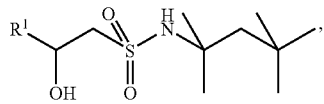

formula VI wherein R¹ has the significance given for formula I, b) dehydrate the compounds of formula VI to give the compounds of formula III,

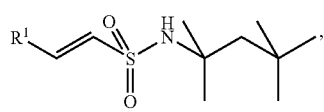

formula III wherein R¹ has the significance given for formula I, c) cleaving the 1,1,3,3-tetramethyl-butyl group of the compounds of formula III to give the free sulfonamides of formula IV,

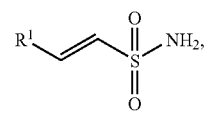

formula IV wherein R¹ has the significance given for formula I, d) reacting the sulfonamides of formula IV with the benzoic acid of formula IX,

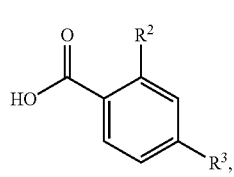

formula IX which is activated before, and wherein R² and R³ have the significance given for formula I, to give the compounds of formula I,

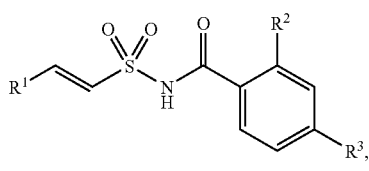

formula I wherein R¹, R² and R³ have the significance given for formula I.

Another embodiment of the invention is a process for the preparation of the compounds of formula I, by reacting a compound of formula IV,

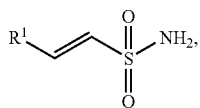

formula IV wherein R¹ has the significance given for formula I;

with the benzoic acid of formula IX,

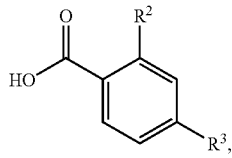

formula IX which is activated before, and wherein R² and R³ have the significance given for formula I to give the compounds of formula I,

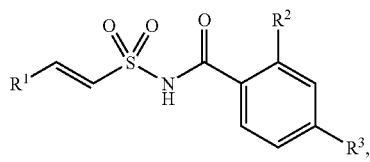

formula I wherein R¹, R² and R³ have the significance given for formula I.

Another embodiment of the invention is a process for the preparation of the compounds of formula I, by reacting a compound of formula VII,

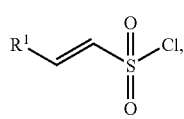

formula VII wherein R¹ has the significance given for formula I, with the benzamide of formula VIII,

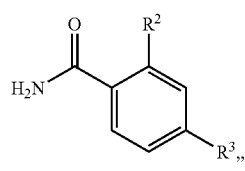

formula VIII wherein R² and R³ have the significance given for formula I to give the compounds of formula I,

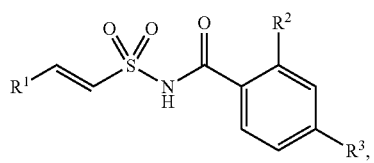

formula I wherein R¹, R² and R³ have the significance given for formula I.

The compounds of formula I, or a pharmaceutically acceptable salt thereof, which are subject of the present invention, may be prepared by any process known to be applicable to the preparation of chemicaly-related compounds. Such processes, when used to prepare a compound of the formula I, or a pharmaceutically-acceptable salt thereof, are illustrated by the following representative schemes 1 to 3 and examples in which, unless otherwise stated, R¹, R² and R³ have the significance given herein before. Necessary starting materials are either commercially available or they may be obtained by standard procedures of organic chemistry. The preparation of such starting materials is e.g. described within the accompanying examples or in the literature cited below with respect to scheme 1 to 3. Alternatively necessary starting materials are obtainable by analogous procedures to those illustrated which are within the ordinary skill of an organic chemist.

The compounds of formula I can be prepared e.g. either according to scheme 1 or the following scheme 2:

Scheme 1

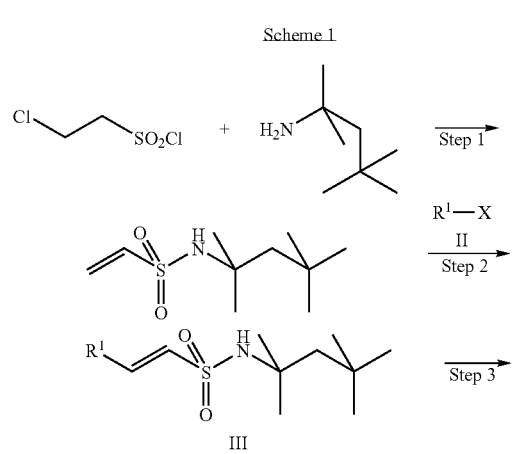

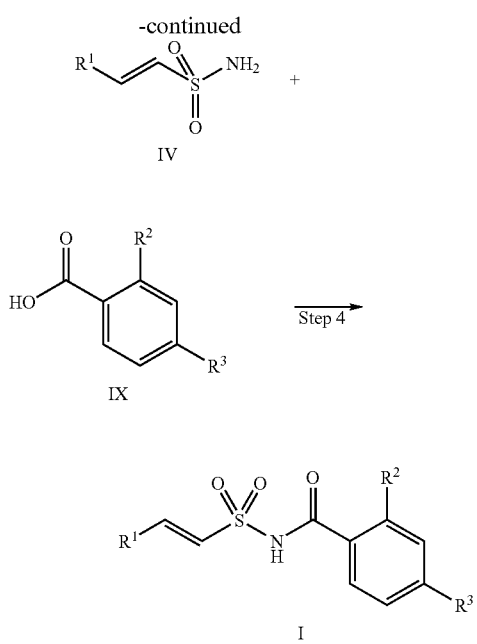

In scheme 1, $R^1$, $R^2$ and $R^3$ have the significance as given above for formula I and X is iodine or bromine.

Step 1:

Step 1 of the reaction sequence (scheme 1) is a one step process involving two chemical transformation (sulfonylation and elimination) in which tert-octylamine is condensed with 2-chloroethane sulfonyl chloride using methods well known to someone skilled in the art, to give ethenesulfonic acid (1,1,3,3-tetramethyl-butyl)-amide. The reaction (sulfonylation and elimination) is typically carried out without solvent, or in solvents like dichloromethane, dichloroethane, acetonitrile, dioxane, tetrahydrofuran, dimethylformamide and mixtures thereof, at temperatures between −78° C. and 30° C. while in the presence or absence of a base such as triethylamine, diisopropylethylamine, potassium carbonate and potassium hydrogen carbonate.

Step 2:

In step 2, scheme 1 ethenesulfonic acid (1,1,3,3-tetramethyl-butyl)-amide is coupled with heteroaryl halides, especially bromides and iodides, of the formula II, using methods well known to someone skilled in the art, e.g. palladium-mediated heteroaryl coupling. The reaction is typically carried out in solvents like dimethylformamide, toluene, dioxane, tetrahydrofuran, and mixtures thereof, at temperatures between 80° C. and 175° C. Typically used bases are cesium carbonate, triethylamine, sodium tert-butoxide and appropriate ligated palladium (0) species can be generated using reagents such as palladium acetate, palladium dichloride, tris(dibenzylideneacetone)dipalladium, bis-triphenylphosphinepalladium dichloride in conjunction with phosphine based ligands such as triphenylphosphine, tri-tolylphosphine and tributylphosphine.

Step 3:

In step 3, scheme 1 the obtained compounds of formula III are converted into their corresponding primary sulfonamides of formula IV, using methods well known to someone skilled in the art like the acidic cleavage of the N-protecting group. The reaction is typically carried out without solvent, or in solvents such as dichloromethane, dichloroethane, acetonitrile, dioxane, chloroform and mixtures thereof, at temperatures between -20° C. and 40° C. Typically used acids are trifluoroacetic acid, aqueous hydrogen chloride, anhydrous hydrogen chloride, sulphuric acid, trifluoromethane sulfonic acid.

Step 4:

Step 4 of the reaction sequence (scheme 1) is a two step process in which activation of the carboxylic group of the benzoic acid of formula IX is followed by acylation of IV, yielding the acylsulfonamide derivatives of formula I. The first step (activation) is typically carried out without solvent, or in solvents like dichloromethane, dichloroethane, tetrahydrofuran, dioxane and mixtures thereof, at temperatures between 0° C. and 100° C. Typical methods used for the activation are chlorination or formation of an imidazolide. Typically used chlorinating reagents are thionylchloride, oxalyl chloride, phosphorus trichloride, phosphorus pentachloride, phosphorus oxychloride, N-chlorosuccinamide triphenylphosphine. A typically used imidazolination method is the reaction with N,N'-carbonyl diimidazole (CDI). Other typically used activation methods include the use of activating agents such as 1-ethyl-3-(3'-dimethylaminopropyl)carbodiimide (EDCI), hydroxy-benzotriazole (HOBt) and the like. The second step (acylation) is typically carried out in solvents like dichloromethane, dichloroethane, acetonitrile, dioxane, tetrahydrofuran, chloroform, dimethylformamide and mixtures thereof, at temperatures between −10° C. and 100° C. Typically used bases are sodium hydride, potassium hydride, potassium carbonate, triethylamine, diisopropylethylamine, and DBU (1,8-diazabicyclo[5.4.0]undec-7-ene.

Procedure for the preparation of compounds of formula I according to scheme 2:

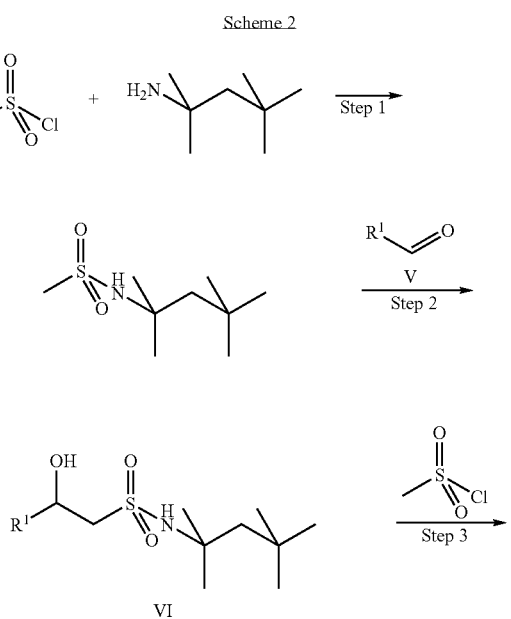

Scheme 2

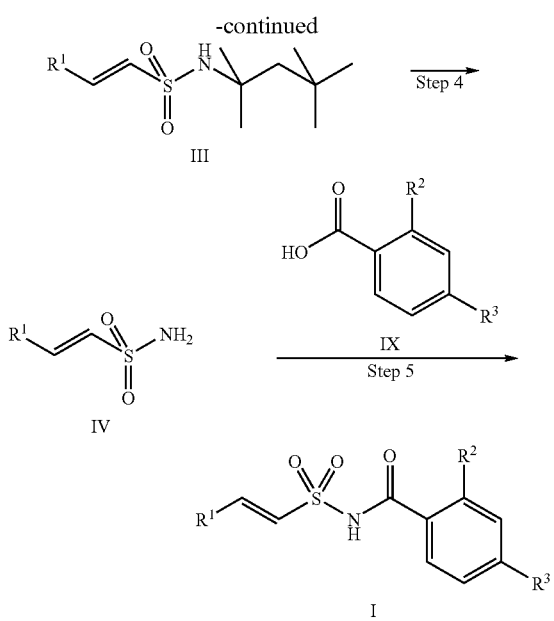

In scheme 2, $R^1$, $R^2$ and $R^3$ have the significance as given above for formula I.

Step 1:

Step 1 of the reaction sequence (scheme 2) is a one step process in which tert-octylamine is condensed with methane sulfonyl chloride using methods well known to someone skilled in the art, to give methanesulfonic acid (1,1,3,3-tetramethyl-butyl)-amide. The reaction (sulfonylation) is typically carried out without solvent, or in solvents like dichloromethane, dichloroethane, acetonitrile, dioxane, tetrahydrofuran, dimethylformamide and mixtures thereof, at temperatures between −78° C. and 30° C. while in the presence or absence of a base such as triethylamine, diisopropylethylamine, potassium carbonate and potassium hydrogen carbonate.

Step 2:

In step 2, scheme 2 methanesulfonic acid (1,1,3,3-tetramethyl-butyl)-amide is coupled with heteroaryl aldehydes of the formula V, using methods well known to someone skilled in the art, to give secondary alcohol of the formula VI. The reaction is typically carried out in solvents like dioxane, tetrahydrofuran, and mixtures thereof, at temperatures between −78° C. and 30° C. while in the presence of a base such as n-butyl lithium, sec-butyl lithium and tert-butyl lithium.

Step 3:

In Step 3, scheme 2 the obtained compounds of formula VI are converted into their corresponding vinyl sulfonamides of formula III (scheme 2) through the condensation/elimination of methane sulfonyl chloride and the alcohol of formula VI using methods well known to someone skilled in the art. The reaction (sulfonylation/elimination) is typically carried out in solvents like dichloromethane, dichloroethane, acetonitrile, dioxane, tetrahydrofuran, dimethylformamide and mixtures thereof, at temperatures between −10° C. and 30° C. while in the presence or absence of a base such as triethylamine, diisopropylethylamine, potassium carbonate and potassium hydrogen carbonate.

Step 4:

In step 4, scheme 2 the obtained compounds of formula III are converted into their corresponding primary sulfonamides of formula IV, using methods well known to someone skilled in the art like the acidic cleavage of the N-protecting group. The reaction is typically carried out without solvent, or in solvents such as dichloromethane, dichloroethane, acetonitrile, dioxane, chloroform and mixtures thereof, at temperatures between −20° C. and 40° C. Typically used acids are trifluoroacetic acid, aqueous hydrogen chloride, anhydrous hydrogen chloride, sulphuric acid, trifluoromethane sulfonic acid.

Step 5:

Step 5 of the reaction sequence (scheme 2) is a two step process in which activation of the carboxylic group of the benzoic acid of formula IX is followed by acylation of IV, yielding the acylsulfonamide derivatives of formula I. The first step (activation) is typically carried out without solvent, or in solvents like dichloromethane, dichloroethane, tetrahydrofuran, dioxane and mixtures thereof, at temperatures between 0° C. and 100° C. Typical methods used for the activation are chlorination or formation of an imidazolide. Typically used chlorinating reagents are thionylchloride, oxalyl chloride, phosphorus trichloride, phosphorus pentachloride, phosphorus oxychloride, N-chlorosuccinamide triphenylphosphine. A typically used imidazolination method is the reaction with N,N'-carbonyl diimidazole (CDI). Other typically used activation methods include the use of activating agents such as 1-ethyl-3-(3'-dimethylaminopropyl)carbodiimide (EDCI), hydroxy-benzotriazole (HOBt) and the like. The second step (acylation) is typically carried out in solvents like dichloromethane, dichloroethane, acetonitrile, dioxane, tetrahydrofuran, chloroform, dimethylformamide and mixtures thereof, at temperatures between −10° C. and 100° C. Typically used bases are sodium hydride, potassium hydride, potassium carbonate, triethylamine, diisopropylethylamine, and DBU (1,8-diazabicyclo [5.4.0]undec-7-ene.

Alternatively, instead of the tert-octyl amino protecting group in formulas III and VI, other suitable amino protecting groups like bis-paramethoxybenzyl or t-butyl (see Harada, H., et al, Bioorg. Med. Chem. 9 (2001) 2955–2968) can be used. The introduction is carried out using the same protocols as provided for step 1 of schemes 1 and 2 (see also Thompson, M. E., J. Org. Chem. 49 (1984) 1700–1703). The removal of the protecting group is carried out using the same protocols as provided for step 3 of scheme 1 and step 4 of scheme 2.

If the heteroaryl ring of $R^1$ in scheme 1 or 2 contains a —NH— (as e.g. pyrrole, imidazole, pyrazole and the like), it is sometimes necessary and well-known to the skilled artisan to use a corresponding N-protecting group like tert-Butyloxycarbonyl (BOC) or tetrahydropyran (THP) and the like during the reaction sequence.

An alternative preparation of compounds IV in scheme 1 or 2 is also described in Harada, H., et al, Bioorg. Med. Chem. 9 (2001) 2955–2968 and Hirooka, S., et al, Bull. Chem. Soc. Jap. 64 (1991) 1431–1433.

Alternatively to schemes 1 to 2 the compounds of formula I can be prepared according to the following reaction sequence shown in scheme 3:

Scheme 3

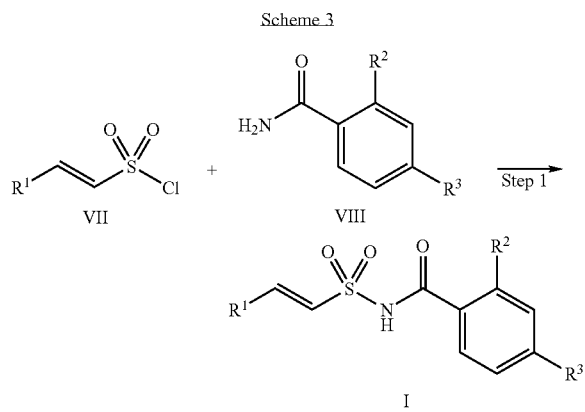

In scheme 3, $R^1$, has the significance as given above for formula I.

Step 1:

In step 1, scheme 3, the sulfonyl chlorides of formula VII are reacted with the benzamides of formula VIII in a N-sulfonylation reaction to yield the compounds of formula I. The reaction is carried e.g. in inert solvents like tetrahydrofuran or dimethylformamide, at temperatures between −80° C. and 50° C. in the presence of a strong base like lithium diisopropylamide, lithium bis(trimethylsilyl)amide, sodium hydride or potassium hydride (e.g. according to Beers, S. A., et al, Bioorg. Med. Chem. 5 (1997) 779–786; U.S. Pat. No. 4,157,257A; Horne, S., et al, J. Chem. Soc. Chem. Commun. 15 (1991) 1046–1048, Borthwick, A. D., et al, J. Med. Chem. 43 (2000) 4452–4464 or Boger, D. L., et al, J. Org. Chem. 55 (1990) 1379–1390).

The sulfonyl chlorides of formula VII can be prepared from the corresponding heteroaryl aldehydes of formula VI according to the procedures of Choi-Sledeski, Y. M., et al, J. Med. Chem. 46 (2003) 681–684 or Wipf, P., et al, Bioorg. Med. Chem. Lett. 11 (2001) 313–317.

Medicaments containing a compound of the present invention or a pharmaceutically acceptable salt thereof and a therapeutically inert carrier are an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

An embodiment of the invention is a pharmaceutical composition, containing one or more compounds according to formula I, together with pharmaceutically acceptable excipients.

Another embodiment of the invention is a pharmaceutical composition, containing one or more compounds according to formula I, for the inhibition of tumor growth.

Another embodiment of the invention is a pharmaceutical composition, containing one or more compounds according to formula I, for the treatment of cancer.

Another embodiment of the invention is a medicament containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of corresponding medicaments for the inhibition of tumor growth.

Another embodiment of the invention is the use of a compound according to formula I, for the manufacture of corresponding medicaments for the treatment of cancer.

Another embodiment of the invention is the use of the compounds of formula I as anti-proliferating agents.

Another embodiment of the invention is the use of one or more compounds of formula I for the treatment of cancer.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic bases or, if the compounds of formula I contain a basic group in $R^1$, from organic or inorganic acids. Examples of base-addition salts include those derived from sodium, potassium, ammonium, quaternary ammonium hydroxides (such as for example, tetramethylammonium hydroxide), especially from sodium. Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Stahl, P. H., and Wermuth, G., (editors), Handbook of Pharmaceutical Salts, Verlag Helvetica Chimica Acta (VHCA), Zurich, (2002) or Bastin, R. J., et al., Organic Proc. Res. Dev. 4 (2000) 427–435.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Pharmacological Activity

The compounds of formula I and their pharmaceutically acceptable salts possess valuable pharmacological properties. It has been found that said compounds show anti-proliferative activity. Consequently the compounds of the present invention are useful in the therapy and/or prevention of proliferative diseases such as cancer. The activity of the present compounds as anti-proliferative agents is demonstrated by the following biological assay:

CellTiter-Glo™ Assay in HCT 116 Cells

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCl1-247) were cultivated in RPMI 1640 medium with GlutaMAX™ I (Invitrogen, Cat-No. 61870-010), 2.5% Fetal Calf Serum (FCS, Sigma Cat-No. F4135 (FBS)); 100

Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the CellTiter-Glo™ assay was done according to the instructions of the manufacturer (CellTiter-Glo™ Luminescent Cell Viability Assay, from Promega). In brief: the cell-plate was equilibrated to room temperature for approximately 30 minutes and than the CellTiter-Glo™ reagent was added. The contents were carefully mixed for 15 minutes to induce cell lysis. After 45 minutes the luminescent signal was measured in Victor 2, (scanning multiwell spectrophotometer, Wallac).

Details:

1st. Day:

Medium: RPMI 1640 with GlutaMAX™ I (Invitrogen, Cat-Nr. 61870), 5% FCS (Sigma Cat.-No. F4135), Pen/Strep (Invitrogen, Cat No. 15140).

HCT116 (ATCC-No. CCl-247): 1000 cells in 60 µl per well of 384 well plate (Greiner 781098, µClear-plate white)

After seeding incubate plates 24 h at 37° C., 5% $CO_2$

2nd. Day: Induction (Treatment with Compounds, 10 Concentrations):

In order to achieve a final concentration of 30 µM as highest concentration 3,5 µl of 10 mM compound stock solution were added directly to 163 µl media. Then step e) of the dilution procedure described below, was followed.

In order to achieve the second highest to the lowest concentrations, a serial dilution with dilution steps of 1:3 was followed according to the procedure (a–e) as described here below:

a) for the second highest concentration add 10 µl of 10 mM stock solution of compound to 20 µl dimethylsulfoxide (DMSO)

b) dilute 8×1:3 (always 10 µl to 20 µl DMSO) in this DMSO dilution row (results in 9 wells with concentrations from 3333.3 µM to 0.51 µM)

c) dilute each concentration 1: 47.6 (3.5 µl compound dilution to 163 µl media)

e) add 10 µl of every concentration to 60 µl media in the cell plate resulting in final concentration of DMSO : 0.3% in every well and resulting in 10 final concentration of compounds ranging from 30 µM to 0.0015 µM.

Each compound is tested in triplicate.

Incubate 120 h (5 days) at 37° C., 5% $CO_2$

Analysis:

Add 30 µl CellTiter-Glo™ Reagent per well, shake 15 minutes at room temperature incubate further 45 minutes at room temperature without shaking Measurement:

Victor 2 scanning multiwell spectrophotometer (Wallac), Luminescence mode (0.5 sec/read, 477 nm)

Determine IC50 using a non-linear curve fit (XLfit software (ID Business Solution Ltd., Guilford, Surrey, UK))

A significant inhibition of HCT 116 cell viability was detected, which is exemplified by the compounds shown in Table 1.

TABLE 1

Results:

| Examples | IC50 HCT 116 [µM] |
|---|---|
| 1-1 | 2.37 |
| 2-1 | 3.41 |
| 2-4 | 5.02 |
| 1-1, 1-3, 1-5, 1-6, 1-8, 1-9, 1-10, 1-11, 2-2, 2-5 2-6, 2-7, 2-9, 2-10, 2-12, 2-14, 2-16, 2-17, 2-18, 2-20, 2-21, 2-22, 2-24, 2-25, 2-26, 2-27, 2-28, 2-29, 17, 3-1, 3-2, 3-4, 3-5, 3-7, 3-9, 3-10, 3-11, 3-13, 3-14, 4-1, 4-2, 4-4, 4-6, 4-7, 4-8, 4-11, 4-12, 4-15, 4-16, 4-17, 4-18, 4-19, 5-1 | 0.50–15.00 |

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragees, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The following examples and references are provided to aid the understanding of the present invention, the true scope of which is set forth in the appended claims. It is understood that modifications can be made in the procedures set forth without departing from the spirit of the invention.

EXPERIMENTAL PROCEDURES

Starting Materials

Preparation of Ethenesulfonic acid (1,1,3,3-tetramethyl-butyl)-amide

2-Chloro-1-ethane sulfonyl chloride (51.3 mL, 0.49 mol) in dichloromethane (400 mL) was added dropwise over 2 hours to a solution of tert-octylamine (236.3 mL, 1.47 mol) and triethylamine (68.3 mL, 0.49 mol) in dichloromethane (400 mL) at −18° C. The mixture temperature was maintained between −18° C. and −9° C. during the addition. The mixture was allowed to warm to ambient temperature over 1 hour then washed with 1N HCl (400 mL) and distilled water (2×200 mL). The organic layer was dried with MgSO$_4$, filtered and concentrated in vacuo to give a pale yellow oil. The oil was dried under vacuum at 50° C. to give ethenesulfonic acid (1,1,3,3-tetramethyl-butyl)-amide, 96.0 g (90% yield) as a pale yellow oil.

$^1$H-NMR (400 MHz; d$^6$-DMSO) 0.98 (9H, s), 1.27 (6H, s), 1.54 (2H, s), 5.84 (1H, d, J=9.8), 5.99 (1H, d, J=16.4), 6.72 (1H, dd, J=16.4, 9.8), 6.90 (1H, s).

Preparation of N-(1,1,3,3-Tetramethyl-butyl)-methanesulfonamide

Methanesulfonyl chloride (46 mL, 0.6 mol) in dichloromethane (100 mL) was added dropwise over 45 minutes to a solution of tert-octylamine (80 mL, 0.5 mol) and triethylamine (84 mL, 0.6 mol) in dichloromethane (400 mL) at 0° C. The mixture was stirred for a further 1 hour at room temperature then 1M HCl (1 L) was added in one portion. The mixture was extracted with dichloromethane (2×1 L). The organic solution was dried over MgSO$_4$, filtered and concentrated in vacuo to afford N-(1,1,3,3-tetramethyl-butyl)-methanesulfonamide as a yellow oil (100.8g, 97%).

$^1$H-NMR (400 MHz; CDCl$_3$) 1.06 (9H, s), 1.47 (6H, s), 1.63 (2H, s), 3.03 (3H, s), 4.36 (1H, br s).

Final Products

Sodium Salt Formation

The final products described below (in Examples 1-1 to 5-1) were obtained either as sulfonamides or as sulfonamide sodium salts depending on the work-up procedures (neutral or acidic HPLC-conditions—for neutral conditions the aqueous eluent is water(pH is 7)/acetonitrile 9:1 and the organic eluent is acetonitrile; for acidic conditions the aqueous eluent is water with 0.2% acetic acid and the organic eluent is acetonitrile with 0.2% acetic acid).

The obtained sulfonamides were or can be converted to their sodium salts using the following procedure:

To a solution of the sulfonamide (1 eq., e.g. 1 mmol) (obtained according to the procedures described below (in Examples 1-1 to 5-1)) in tetrahydrofurane (e.g. 10 ml), 1 eq. (e.g. 1 mmol) sodium methoxide (25% solution in methanol) was added and the mixture was stirred at room temperature for 1 hour. The tetrahydrofurane was removed in vacuo and the residue suspended in diethyl ether (e.g. 50 to 100 ml) and heated to reflux four 1 hour, cooled down to room temperature filtered off and dried.

Example 1-1

(E)-2-Thiophen-2-yl-ethenesulfonic acid 2,4-dichloro-benzoylamide i) (E)-2-Thiophen-2-yl-ethenesulfonic acid (1,1,3,3-tetramethyl-butyl)-amide Palladium acetate (169 mg, 0.75 mmol) and triphenylphosphine (420 mg, 1.6 mmol) were added to a solution of ethenesulfonic acid (1,1,3,3-tetramethyl-butyl)-amide (10 g, 45.7 mmol) and 2-bromo-thiophene (3.74 mL, 39.1 mmol) in N,N-dimethylformamide (75 mL). Triethylamine (14.7 mL, 105.5 mmol) was added and the mixture was flushed with nitrogen and heated at 140° C. for 16 hours. The mixture was cooled to room temperature and 1N HCl (250 mL) was added in one portion. The mixture was extracted with ethyl acetate (3×200 mL) and the combined organics were dried over MgSO$_4$, filtered and concentrated in vacuo to afford a solid. The solid was purified by dry flash chromatography (SiO$_2$, heptane to 1:1 heptane: ethyl acetate). The fractions were combined to afford (E)-2-thiophen-2-yl-ethenesulfonic acid (1,1,3,3-tetramethyl-butyl)-amide (2.5g, 21% yield).

MS(ESI+): M=365 (M+Na+acetonitrile), 625 (2M+Na)
$^1$H-NMR (400 MHz; d$^4$-MeOD): 1.26 (9H, s), 1.59 (6H, s), 1.85 (2H, s), 6.94 (1H, d, J=15.3), 7.31 (1H, dd, J=5.12, 3.65), 7.57–7.58 (1H, m), 7.69–7.73 (1H, m), 7.75–7.77 (1H, m).

ii) (E)-2-Thiophen-2-yl-ethenesulfonic acid amide (E)-2-Thiophen-2-yl-ethenesulfonic acid (1,1,3,3-tetramethyl-butyl)-amide (5.17 g, 17.2 mmol) was stirred for 15 minutes in a 1:1 mixture of trifluoroacetic acid and dichloromethane (40 mL). The mixture was concentrated in vacuo to afford a solid that was washed with dichloromethane (10 mL) in heptane (100 mL). The resultant solid was collected by suction filtration and dried under vacuum at ambient temperature to afford (E)-2-thiophen-2-yl-ethenesulfonic acid amide (2.89 g, 89%).

MS(ESI+): M=173(M-NH$_2$), 109 (M-SO$_2$NH$_2$).
$^1$H-NMR (400 MHz; d$^4$-MeOD): 7.08–7.12 (1H, d, J=15.5), 7.33–7.38 (1H, m), 7.60–7.62 (1H, m), 7.78–7.82 (2H, m).

iii) (E)-2-Thiophen-2-yl-ethenesulfonic acid 2,4-dichloro-benzoylamide 2,4-Dichlorobenzoyl chloride (53 μL, 0.375 mmol) was added to a mixture of potassium carbonate (69 mg, 0.5 mmol) and (E)-2-thiophen-2-yl-ethenesulfonic acid amide (47 mg, 0.25 mmol) in 1,4-dioxane (1.5 mL) at ambient temperature. The mixture was heated at 80° C. for 16 hours then allowed to cool to room temperature whereupon 1N HCl (2 mL) was added in one portion. The mixture was extracted with ethyl acetate (2 mL) and the organics were dried with MgSO$_4$, filtered and concentrated in vacuo. The resultant residue was purified by preparative HPLC to afford (E)-2-thiophen-2-yl-ethenesulfonic acid 2,4-dichloro-benzoylamide (26.3 mg, 29%).

MS(ESI+): M=362(M+H), 745(2M+Na)

$^1$H-NMR: (400 MHz, d$^6$-DMSO): 7.17 (d, J=15.1 Hz, 1H), 7.20 (dd, J=3.7, 5.0 Hz, 1H), 7.52 (dd, J=8.3, 2.0 Hz, 1H), 7.61 (d, J=8.3 Hz, 1H), 7.71 (d, J=3.7 Hz, 1H), 7.74 (d, J=1.9 Hz, 1H), 7.84 (d, J=15.1 Hz, 1H), 7.84 (d, J=5.0 Hz, 1H) 12.61 (br. s, 1H)

The following examples were prepared in an analogous manner as described for example 1-1 using the appropriate starting material:

| Example No. | Systematic Name | MS (M+H) | $^1$H-NMR |
|---|---|---|---|
| 1-2 | (E)-2-Thiophen-3-yl-ethenesulfonic acid 2,4-dichloro-benzoylamide | 362.0(ESI+) | (400MHz, d$^6$-DMSO): 7.34(d, J=15.3Hz, 1H), 7.52(dd, J=8.2, 1.8Hz, 1H), 7.59(d, J=8.3Hz, 1H), 7.65(m, 3H), 7.73(d, J=1.7Hz, 1H), 8.16(d, J=2.1Hz, 1H), 12.54(br. s, 1H) |
| 1-3 | (E)-2-Thiophen-3-yl-ethenesulfonic acid 2-chloro-4-fluoro-benzoylamide; sodium salt | 346.2(ESI+) | (400MHz, d$^6$-DMSO): 7.60(m, 1H, thiophen-2-H), 7.42(m, 2H, phenyl-3-H, phenyl-5-H), 7.22(m, 1H, phenyl-6-H), 7.09(m, 1H, thiophen-5-H), 7.05(d, 1H, ethene), 6.97(d, 1H, ethene, J=15.65Hz, trans), 6.94(m, 1H, thiophene-4-H) |
| 1-4 | (E)-2-Thiophen-2-yl-ethenesulfonic acid 2-chloro-4-fluoro-benzoylamide; sodium salt | 346.2(ESI+) | (400MHz, d$^6$-DMSO): 7.37(m, 2H, thiophen-5-H, phenyl-6-H), 7.12(m, 2H, thiophen-4-H, ethene), 7.04(m, 1H, phenyl-3-H), 6.89(m, 3H, thiophen-3-H, phenyl-5-H, ethene) |
| 1-5 | (E)-2-Thiophen-3-yl-ethenesulfonic acid 4-fluoro-2-trifluoromethyl-benzoylamide; sodium salt | 380.2(ESI+) | (400MHz, d$^6$-DMSO): 7.50(s, 1H, thiophene2-H), 7.35(m, 2H, thiophene-5-H, phenyl-6-H), 7.19(m, 2H, phenyl-3-H, phenyl-5-H), 7.12(d, 1H, thiophene-4-H), 6.96(d, 1H, ethene), 6.88(d, 1H, ethene, J=15.70Hz, trans) |
| 1-6 | (E)-2-Thiophen-3-yl-ethenesulfonic acid 2,4-bis-trifluoromethyl-benzoylamide; sodium salt | 430.2(ESI+) | (400MHz, d$^6$-DMSO): 7.83(d, 1H, phenyl-6-H), 7.76(s, 1H, phenyl-3-H), 7.64(s, 1H, thiophene-2-H), 7.59(d, 1H, phenyl-5-H), 7.45(m, 1H, thiophene-5-H), 7.25(m, 1H, thiophene-4-H), 7.10(d, 1H, ethene), 6.99(d, 1H, ethene, J=15.65Hz, trans) |
| 1-7 | (E)-2-Thiophen-2-yl-ethenesulfonic acid 2,4-bis-trifluoromethyl-benzoylamide; sodium salt | 430.2(ESI+) | (400MHz, d$^6$-DMSO): 7.74(d, 1H, phenyl-6-H), 7.67(s, 1H, phenyl-3-H), 7.50(d, 1H, phenyl-5-H), 7.37(m, 1H, thiophene-5-H), 7.14(m, 2H, thiophene-4-H, ethene), 6.82(d, 1H, ethene, J=15.65Hz, trans), 6.88(m, 1H, thiophene-3-H) |
| 1-8 | (E)-2-(5-Methyl-thiophen-2-yl)-ethenesulfonic acid 2,4-dichloro-benzoylamide | 375.8(ESI+) | (400MHz, d$^6$-DMSO): 12.53(br. s, 1H), 7.74(d, J=15.3Hz, 1H), 7.73(d, J=1.8Hz, 1H), 7.60(d, J=8.1Hz, 1H), 7.52(dd, J=8.1, 1.8Hz, 1H), 7.51(obs., 1H), 6.98(d, J=15.3Hz, 1H), 6.91(d, J=2.5Hz, 1H), 2.49(s, 3H) |
| 1-9 | (E)-2-(3-Methyl-thiophen-2-yl)-ethenesulfonic acid 2,4-dichloro-benzoylamide | 375.9(ESI+) | (400MHz, d$^6$-DMSO): 12.57(br. s, 1H), 7.77–7.71(m, 3H), 7.61(d, J=8.3Hz, 1H), 7.53(dd, J=8.2, 1.8Hz, 1H, 7.06(d, J=5.0Hz, 1H), 6.99(d, J=15.2Hz, 1H), 2.34(s, 3H) |
| 1-10 | (E)-2-(4-Methyl-thiophen-2-yl)-ethenesulfonic acid 2,4-dichloro-benzoylamide | 374.08(ESI+) | (400MHz, d$^6$-DMSO): 12.58(br, 1H), 7.76(d, 14.2Hz, 1H), 7.74(d, 2.0Hz, 1H), 7.61(d, 8.3Hz, 1H), 7.53(dd, 7.3Hz, 1.9Hz, 1H), 7.52(s, 1H), 7.43(s, 1H), 7.10(d, 15.1Hz, 1H), 2.23(s, 3H) |

-continued

| Example No. | Systematic Name | MS (M+H) | $^1$H-NMR |
|---|---|---|---|
| 1-11 | (E)-2-(3,5-Dimethyl-isoxazol-4-yl)-ethenesulfonic acid 2,4-dichloro-benzoylamide; sodium salt | | (400MHz, d$^6$-DMSO): 7.51(d, 8.1Hz, 1H), 7.51(d, 2.3Hz, 1H), 7.35(dd, 8.3Hz, 2.0Hz, 1H), 7.04(t, 16.6Hz, 1H), 2.47(s, 3H), 2.30(s, 3H) |

Example 2-1

(E)-2-Pyridin-3-yl-ethenesulfonic acid 2,4-dichloro-benzoylamide; sodium salt i) 2-Hydroxy-2-pyridin-3-yl-ethanesulfonic acid (1,1,3,3-tetramethyl-butyl)-amide nButyl lithium (1.6M in hexanes) (31.3 mL, 50 mmol) was added dropwise to N-(1,1,3,3-tetramethyl-butyl)-methanesulfonamide (5.23 g, 25 mmol) in tetrahydrofuran (30 mL) at −78° C. under an atmosphere of nitrogen. The mixture was warmed to 0° C. for 30 minutes then cooled to −78° C. 3-Pyridine carboxaldehyde (2.4 mL, 25 mmol) in tetrahydrofuran (20 mL) was added dropwise to the mixture over 20 minutes and the mixture was warmed to room temperature and stirred for a further 1 hour. Water (100 mL) was added to the reaction mixture and the whole was extracted with ethyl acetate (2×100 mL). The combined organics were dried over MgSO$_4$, filtered and concentrated in vacuo to afford a pale yellow solid. The solid was washed with dichloromethane (10 mL) in heptane (100 mL) to afford 2-hydroxy-2-pyridin-3-yl-ethanesulfonic acid (1,1,3,3-tetramethyl-butyl)-amide as a pale yellow solid (5.67 g, 72%).

MS (ESI+): M=315 (M+H)

$^1$H-NMR (400 MHz; d$^4$-MeOD): 1.01 (9H, s), 1.37 (6H, s), 1.62 (2H, s), 3.34–3.38 (1H, m), 3.45–3.51 (1H, m), 5.19–5.22 (1H, m), 7.40–7.43 (1H, m), 7.86–7.89 (1H, m), 8.44 (1H, dd, J=1.5, 4.9), 8.55 (1H, d, J=2.4).

ii) (E)-2-Pyridin-3-yl-ethenesulfonic acid (1,1,3,3-tetramethyl-butyl)-amide

Methanesulfonyl chloride (2.1 mL, 27 mmol) in dichloromethane (10 mL) was added dropwise over 15 minutes to a solution of 2-hydroxy-2-pyridin-3-yl-ethanesulfonic acid (1,1,3,3-tetramethyl-butyl)-amide (5.67 g, 18 mmol) and triethylamine (15 mL, 108 mmol) in dichloromethane (40 mL) at 0° C. The mixture was warmed to ambient temperature and stirred for a further 1 hour. Water (50 mL) was added in one portion to the reaction mixture and the whole was extracted with dichloromethane (2×50 mL). The organic solution was dried over MgSO$_4$, filtered and concentrated in vacuo. The residue was purified by chromatography (SiO$_2$, ethyl acetate:heptane 1:1 to ethyl acetate) to afford (E)-2-pyridin-3-yl-ethenesulfonic acid (1,1,3,3-tetramethyl-butyl)-amide as a pale yellow solid (3.91 g, 73%).

MS(ESI+): M=297 (M+H)

$^1$H-NMR (400 MHz; CDCl$_3$): 0.87 (9H, s), 1.26 (6H, s), 1.45 (2H, s), 4.16 (1H, br s), 6.72 (1H, d, J=15.7), 7.16–7.19 (1H, m), 7.26 (1H, d, J=15.7), 7.59–7.62 (1H, m), 8.45–8.46 (1H, m), 8.54 (1H, m).

iii) (E)-2-Pyridin-3-yl-ethenesulfonic acid amide (E)-2-pyridin-3-yl-ethenesulfonic acid (1,1,3,3-tetramethyl-butyl)-amide (3.63 g, 12.3 mmol) was stirred for 3 hours in a 1:1 mixture of trifluoroacetic acid and dichloromethane (40 mL). The solvent was concentrated in vacuo to afford a yellow oil. The oil was dissolved in dichloromethane (50 mL) and washed with saturated sodium bicarbonate solution (50 mL), dried over MgSO$_4$, filtered and concentrated in vacuo to afford (E)-2-pyridin-3-yl-ethenesulfonic acid amide as a pale yellow solid (1.65 g, 73%).

MS(ESI+): M=185 (M+H)

$^1$H-NMR (400 MHz; d$^4$-MeOD): 7.41 (1H, d, J=15.7), 7.55–7.61 (2H, m), 8.18–8.21 (1H, m), 8.64–8.66 (1H, m), 8.82–8.83 (1H, m).

iv) (E)-2-Pyridin-3-yl-ethenesulfonic acid 2,4-dichloro-benzoylamide; sodium salt Sodium hydride (60% dispersion in mineral oil) (36 mg, 0.9 mmol) was added to a solution of (E)-2-Pyridin-3-yl-ethenesulfonic acid amide (56 mg, 0.3 mmol) in dioxane (1 mL) and the mixture was shaken for 30 minutes. A solution of 2,4-dichlorobenzoyl chloride (63 μL, 0.45 mmol) in dioxane (0.5 mL) was added to the mixture and the whole was shaken at room temperature for 18 hours. Water (0.1 mL) was added to the mixture and the whole was concentrated in vacuo. The resultant residue was purified by preparative HPLC to give (E)-2-pyridin-3-yl-ethenesulfonic acid 2,4-dichloro-benzoylamide (29.1 mg, 26%) as sodium salt.

MS(ESI+): M=357 (M+H), 398 (M+CH$_3$CN), 713 (2M+H)

$^1$H-NMR (400 MHz, d$^6$-DMSO): 7.23 (d, J=15.4 Hz, 1H), 7.33 (dd, J=8.0, 2.1 Hz, 1H), 7.35 (m, 1H), 7.47 (d, J=1.9 Hz, 1H), 7.54 (d, J=8.3 Hz, 1H), 7.60 (d, J=7.7 Hz, 1H), 7.66 (d, J=15.4 Hz, 1H), 7.82 (ddd, 7.7, 7.7, 1.9 Hz, 1H), 8.59 (m, 1H)

The following examples were prepared in an analogous manner as described for example 2-1 using the appropriate starting material:

| Example No. | Systematic Name | MS (M+H) | ¹H-NMR |
|---|---|---|---|
| 2-2 | (E)-2-Pyridin-2-yl-ethenesulfonic acid 2,4-dichloro-benzoylamide; sodium salt | 357.0(ESI+) | (400MHz, d⁶-DMSO): 7.23(d, J=15.8Hz, 1H), 7.33(dd, J=8.3, 2.0Hz, 1H), 7.45(m, 3H), 7.53(d, J=8.3Hz, 1H), 8.03(ddd, J=8.0, 2.0, 1.5Hz, 1H), 8.53(dd, J=4.8, 1.5Hz, 1H), 8.73(d, J=2.0Hz, 1H) |
| 2-3 | (E)-2-Pyridin-4-yl-ethenesulfonic acid 2,4-dichloro-benzoylamide; sodium salt | 357.0(ESI+) | (400MHz, d⁶-DMSO): 7.17(d, J=15.8Hz, 1H), 7.33(dd, J=8.2, 2.0Hz, 1H), 7.41(d, J=2.0Hz, 1H), 7.54(m, 4H), 8.58(m, 2H) |
| 2-4 | (E)-2-(6-Methoxy-pyridin-3-yl)-ethenesulfonic acid 2,4-dichloro-benzoylamide; sodium salt | 387.0(ESI+) | (400MHz, d⁶-DMSO): 3.87(s, 3H), 6.84(d, J=8.7Hz, 1H), 7.18(d, J=15.8Hz, 1H), 7.27(d, J=15.8Hz, 1H), 7.33(dd, J=8.2, 2.0Hz, 1H), 7.46(d, J=2.0Hz, 1H), 7.52(d, J=8.3Hz, 1H), 7.98(dd, J=8.7, 2.5Hz, 1H), 8.32(d, J=2.4Hz, 1H) |
| 2-5 | (E)-2-(6-Methyl-pyridin-2-yl-ethenesulfonic acid 2,4-dichloro-benzoylamide; sodium salt | 371.0(ESI+) | (400MHz, d⁶-DMSO): 2.52,(s, 3H), 7.19(d, J=15.3Hz, 1H), 7.21(d, J=7.3Hz, 1H), 7.34(dd, J=8.3, 2.0Hz, 1H), 7.39(d, J=7.6Hz, 1H), 7.47(d, J=2.0Hz, 1H), 7.55(d, J=8.2Hz, 1H), 7.63(d, J=15.4Hz, 1H), 7.71(dd, J=7.7, 7.7, 1H) |
| 2-6 | (E)-2-Pyridin-2-yl-ethenesulfonic acid 2-chloro-4-fluoro-benzoylamide; sodium salt | 341.0(ESI+) | (400MHz, d⁶-DMSO): 8.35(m, 1H, pyridyl-6-H), 7.57(m, 1H, pyridyl-4-H), 7.43(d, 1H, ethene), 6.97(d, 1H, ethene, J=15.30Hz, trans), 7.35(m, 2H, phenyl-6-H, pyridyl-3-H), 7.10(m, 1H, pyridyl-5-H), 7.00(m, 1H, phenyl-3-H), 6.86(m, 1H, phenyl-5-H) |
| 2-7 | (E)-2-Pyridin-2-yl-ethenesulfonic acid 4-fluoro-2-trifluoromethyl-benzoylamide; sodium salt | 375.0(ESI+) | (400MHz, d⁶-DMSO): 8.41(m, 1H, pyridyl-6-H), 7.62(m, 1H, pyridyl-4-H), 7.41(m, 3H, phenyl 3-H, pyridyl-3-H, ethene), 7.01(d, 1H, ethene, J=15.30Hz, trans), 7.25(m, 2H, phenyl-5-H, phenyl-6-H), 7.15(m, 1H, pyridyl-5-H) |
| 2-8 | (E)-2-Pyridin-3-yl-ethenesulfonic acid 2-chloro-4-fluoro-benzoylamide; sodium salt | 341.0(ESI+) | (400MHz, d⁶-DMSO): 8.51(s, 1H, pyridyl-2-H), 8.31(m, 1H, pyridyl-6-H), 7.81(d, 1H, pyridyl-4-H), 7.38(m, 1H, phenyl-6-H), 7.20(m, 2H, pyridyl-5-H, ethene), 7.02(m, 2H, phenyl-3-H, ethene), 6.89(m, 1H, phenyl-5-H) |
| 2-9 | (E)-2-Pyridin-3-yl-ethenesulfonic acid 4-fluoro-2-trifluoromethyl-benzoylamide; sodium salt | 375.0(ESI+) | (400MHz, d⁶-DMSO): 8.54(s, 1H, pyridyl-2-H), 8.35(m, 1H, pyridyl-6-H), 7.83(m, 1H, pyridyl-4-H), 7.46(m, 1H, phenyl-6-H), 7.26(m, 4H, pyridyl-5-H, phenyl-3-H, phenyl-5-H, ethene), 7.06(d, 1H, ethene, J=17.05Hz, trans) |
| 2-10 | (E)-2-(6-Methoxy-pyridin-3-yl)-ethenesulfonic acid 2-chloro-4-fluoro-benzoylamide; sodium salt | 371.0(ESI+) | (400MHz, d⁶-DMSO): 8.09(s, 1H, pyridyl-2-H), 7.74(m, 1H, pyridyl-4-H), 7.37(m, 1H, phenyl-6-H), 7.36(m, 2H, phenyl-3-H, ethene), 6.95(d, 1H, ethene, J=15.30Hz, trans), 6.87(m, 1H, phenyl-5-H), 6.62(d, 1H, pyridyl-5-H), 3.66(s, 3H, methoxy) |
| 2-11 | (E)-2-(6-Methoxy-pyridin-3-yl)-ethenesulfonic acid 4-fluoro-2-trifluoromethyl-benzoylamide; sodium salt | 405.0(ESI+) | (400MHz, d⁶-DMSO): 8.14(s, 1H, pyridyl-2-H), 7.78(m, 1H, pyridyl-4-H), 7.44(m, 1H, phenyl-6-H), 7.27(m, 2H, phenyl-3-H, phenyl-5-H, 7.08(d, 1H, ethene), 7.00(d, 1H, ethene, J=16.45Hz, trans), 6.68(d, 1H, pyridyl-5-H), 3.72(s, 3H, methoxy) |
| 2-12 | (E)-2-(6-Methoxy-pyridin-3-yl)-ethenesulfonic acid 2,4-bis-trifluoromethyl- | 345.2(ESI+) | (400MHz, d⁶-DMSO): 8.16(s, 1H, phenyl-3-H), 7.79(m, 2H, phenyl-6-H, pyridyl-4-H), 7.72(s, 1H, pyridyl-2-H), 7.55(m, 1H, phenyl-5-H), 7.09(d, 1H, ethene), 7.03(d, 1H, ethene, J=14.90Hz, trans), |

-continued

| Example No. | Systematic Name | MS (M+H) | ¹H-NMR |
|---|---|---|---|
| | benzoylamide; sodium salt | | 6.69(d, 1H, pyidyl-5-H) |
| 2-13 | (E)-2-Pyridin-2-yl-ethenesulfonic acid 2,4-bis-trifluoromethyl-benzoylamide; sodium salt | 425.0(ESI+) | (400MHz, d⁶-DMSO): 8.41(m, 1H, pyridyl-6-H), 7.76(d, 1H, phenyl-6-H), 7.70(s, 1H, phenyl-3-H), 7.62(m, 1H, pyridyl-4-H), 7.53(m, 1H, phenyl-5-H), 7.46(d, 1H, ethene), 7.03(d, 1H, ethene, J=15.30Hz, trans), 7.39(d, 1H, pyridyl-3-H), 7.15(m, 1H, pyridyl-5-H) |
| 2-14 | (E)-2-Pyridin-3-yl-ethenesulfonic acid 2,4-bis-trifluoromethyl-benzoylamide; sodium salt | 425.0(ESI+) | (400MHz, d⁶-DMSO): 8.58(s, 1H, pyridyl-2-H), 8.39(m, 1H, pyridyl-6-H), 7.86(d, 1H, pyridyl-4-H), 7.81(d, 1H, phenyl-6-H), 7.74(s, 1H, phenyl-3-H), 7.58(d, 1H, phenyl-5-H), 7.27(m, 2H, pyridyl-5-H, ethene), 7.10(d, 1H, ethene) |
| 2-15 | (E)-2-(6-Methyl-pyridin-2-yl)-ethenesulfonic acid 4-fluoro-2-trifluoromethyl-benzoylamide; sodium salt | 389.0(ESI+) | (400MHz, d⁶-DMSO): 7.48(m, 1H, phenyl-6-H, 7.40(m, 2H, phenyl-3-H, ethene), 6.95(d, 1H, ethene, J=14.15Hz, trans), 7.23(m, 2H, phenyl-5-H, pyridyl-4-H), 7.15(d, 1H, pyridyl-3-H), 6.99(d, 1H, pyridyl-5-H), 2.35(s, 3H, methyl) |
| 2-16 | (E)-2-(6-Methyl-pyridin-2-yl)-ethenesulfonic acid 2,4-bis-trifluoromethyl-benzoylamide; sodium salt | 457.1(ESI+) | (400MHz, d⁶-DMSO): 7.79(m, 1H, phenyl-6-H), 7.72(s, 1H, phenyl-3-H), 7.54(m, 2H, phenyl-5-H, pyridyl-4-H), 7.43(d, 1H, ethene, J=15.30Hz, trans), 7.20(d, 1H, pyridyl-3-H), 7.02(m, 2H, pyridyl-5-H, ethene), 2.35(s, 3H, methyl) |
| 2-17 | (E)-2-Pyridin-3-yl-ethenesulfonic acid 2,4-bis-trifluoromethyl-benzoylamide | 425.2(ESI+) | (400MHz, d⁶-DMSO): 7.54(dd, 7.8Hz, 4.8Hz, 1H); 7.72(d, 15.7Hz, 1H); 7.76(d, 16.4Hz, 1H); 7.96(d, 7.8Hz, 1H); 8.19(s, 1H); 8.20(d, 8.3Hz, 1H); 8.30(dd, 8.1Hz, 1.9Hz, 1H); 8.67(dd, 4.8Hz, 1.3Hz, 1H); 8.98(d, 2.0Hz, 1H) |
| 2-18 | (E)-2-Pyrimidin-5-yl-ethenesulfonic acid 2,4-dichloro-benzoylamide; sodium salt | 357.9(API+) | (400MHz, d⁶-DMSO): 7.22(d, 15.9Hz, 1H); 7.33(dd, 8.3Hz, 2.0Hz, 1H); 7.47(d, 2.0Hz, 1H); 7.54(d, 8.3Hz, 1H); 7.58(d, 15.9Hz, 1H); 9.05(s, 2H), 9.12(s, 1H) |
| 2-19 | (E)-2-(6-Trifluoromethyl-pyridin-3-yl)-ethenesulfonic acid 2,4-dichloro-benzoylamide; sodium salt | 424.9(API+) | 7.33(d, 15.4Hz, 1H); 7.34(dd, 8.6Hz., 2.0Hz, 1H); 7.47(d, 2.0Hz. 1H); 7.54(d, 8.3Hz, 1H); 7.61(d, 15.9Hz, 1H); 7.91(d, 8.3Hz, 1H); 8.33(dd, 8.3Hz, 2.0Hz, 1H), 8.97(d, 2.0Hz, 1H) |
| 2-20 | (E)-2-(6-Chloro-pyridin-3-yl)-ethenesulfonic acid 2,4-dichloro-benzoylamide; sodium salt | 391.8(API+) | (400MHz, d⁶-DMSO): 7.22(d, 15.7Hz, 1H); 7.33(dd, 8.3Hz, 2.0Hz, 1H); 7.46(d, 2.3Hz, 1H); 7.47(d, 15.9Hz, 1H); 7.53(d, 8.3Hz, 2H); 8.12(dd, 8.3Hz, 2.5Hz, 1H); 8.60(d, 2.3Hz, 1H) |
| 2-21 | (E)-2-(2-Chloro-pyridin-3-yl)-ethenesulfonic acid 2,4-dichloro-benzoylamide; sodium salt | 391.1(ESI+) | (400MHz, d⁶-DMSO): 7.22(d, 15.7Hz, 1H); 7.33(dd, 8.3Hz, 2.0Hz, 1H); 7.46(d, 2.0Hz, 1H); 7.47(d, 15.9Hz, 1H), 7.53(d, 8.3Hz, 2H); 8.12(dd, 8.3Hz, 2.5Hz, 1H); 8.60(d, 2.3Hz, 1H) |
| 2-22 | (E)-2-Thiazol-2-yl-ethenesulfonic acid 2,4-dichloro-benzoylamide; sodium salt | 362.8(API+) | (400MHz, d⁶-DMSO): 7.32(d, 15.9Hz, 1H); 7.34(dd, 8.1Hz, 2.3Hz, 1H), 7.48(d, 2.3Hz, 1H); 7.51(d, 14.9Hz, 1H), 7.54(d, 8.1Hz, 1H); 7.83(d, 3.3Hz, 1H); 7.93(d, 3.3Hz, 1H) |

-continued

| Example No. | Systematic Name | MS (M+H) | ¹H-NMR |
|---|---|---|---|
| 2-23 | (E)-2-(4-Bromo-thiophen-2-yl)-ethenesulfonic acid 2,4-dichloro-benzoylamide; sodium salt | 441.9(ESI+) | (400MHz, d⁶-DMSO): 7.11(d, 15.7Hz, 1H); 7.31(d, 15.4Hz, 1H); 7.33(dd, 8.3Hz, 2.3Hz, 1H); 7.43(d, 1.3Hz, 1H); 7.47(d, 2.0Hz, 1H); 7.52(d, 8.3Hz, 1H); 7.71(d, 1.0Hz, 1H) |
| 2-24 | (E)-2-(3-Bromo-thiophen-2-yl)-ethenesulfonic acid 2,4-dichloro-benzoylamide; sodium salt | 441.9(ESI+) | (400MHz, d⁶-DMSO): 7.16(d, 15.7Hz, 1H); 7.19(d, 5.3Hz, 1H); 7.30(d, 14.9Hz, 1H); 7.33(dd, 8.1Hz, 2.3Hz, 1H); 7.47(d, 2.0Hz, 1H); 7.53(d, 8.3Hz, 1H); 7.74(d, 5.3Hz, 1H) |
| 2-25 | (E)-2-(6-Methyl-pyridin-2-yl)-ethenesulfonic acid 2-chloro-4-fluoro-benzoylamide; sodium salt | 355.3(API+) | |
| 2-26 | (E)-2-Benzo[b]thiophen-3-yl-ethenesulfonic acid 2-chloro-4-fluoro-benzoylamide; sodium salt | 396.8(ESI+) | (400MHz, d⁶-DMSO): 8.10(s, 1H), 8.09(d, J=7.7Hz, 1H), 8.05(d, J=7.7Hz, 1H), 7.63(t, J=7.5Hz, 1H), 7.57–7.48(m, 4H), 7.30(dd, J=7.8, 1.8Hz, 1H), 7.15(t, J=7.5Hz, 1H) |
| 2-27 | (E)-2-Benzo[b]thiophen-3-yl-ethenesulfonic acid 2,4-dichloro-benzoylamide; sodium salt | 413.4(ESI+) | (400MHz, d⁶-DMSO): 8.18(s, 1H), 8.09(d, J=8.0Hz, 1H), 8.05(d, J=8.0Hz, 1H), 7.59–7.46(m, 6H), 7.36(dd, J=8.0, 1.6Hz, 1H) |
| 2-28 | (E)-2-Benzo[b]thiophen-3-yl-ethenesulfonic acid 4-fluoro-2-trifluoromethyl-benzoylamide; sodium salt | 430.5(ESI+) | (400MHz, d⁶-DMSO): 8.15(s, 1H), 8.09(d, J=8.0Hz, 1H), 8.05(d, J=7.7Hz, 1H), 7.66(t, J=7.4Hz, 1H), 7.55–7.44(m, 6H) |
| 2-29 | (E)-2-Benzo[b]thiophen-3-yl-ethenesulfonic acid 2,4-ditrifluoromethyl-benzoylamide; sodium salt | 480.4(ESI+) | (400MHz, d⁶-DMSO): 8.17(s, 1H), 8.09(d, J=7.6Hz, 1H), 8.05(d, J=8.0Hz, 1H), 8.00(d, J=8.8Hz, 1H), 7.93(s, 1H), 7.76(d, J=8.0Hz, 1H), 7.55–7.44(m, 4H) |

Example 3-1

(E)-2-Thiophen-2-yl-ethenesulfonic acid 4-chloro-2-methoxy-benzoylamide; sodium salt i) (E)-2-Thiophen-2-yl-ethenesulfonic acid (1,1,3,3-tetramethyl-butyl)-amide Palladium acetate (169 mg, 0.75 mmol) and triphenylphosphine (420 mg, 1.6 mmol) were added to a solution of ethenesulfonic acid (1,1,3,3-tetramethyl-butyl)-amide (10 g, 45.7 mmol) and 2-bromo-thiophene (3.74 mL, 39.1 mmol) in N,N-dimethylformamide (75 mL). Triethylamine (14.7 mL, 105.5 mmol) was added and the mixture was flushed with nitrogen and heated at 140° C. for 16 hours. The mixture was cooled to room temperature and 1N HCl (250 mL) was added in one portion. The mixture was extracted with ethyl acetate (3×200 mL) and the combined organics were dried over MgSO₄, filtered and concentrated in vacuo to afford a solid. The solid was purified by dry flash chromatography (SiO₂, heptane to 1:1 heptane: ethyl acetate). The fractions were combined to afford (E)-2-thiophen-2-yl-ethenesulfonic acid (1,1,3,3-tetramethyl-butyl)-amide (2.5 g, 21% yield).

MS(ESI+): M=365 (M+Na+acetonitrile), 625 (2M+Na)

¹H-NMR (400 MHz; d⁴-MeOD): 1.26 (9H, s), 1.59 (6H, s), 1.85 (2H, s), 6.94 (1H, d, J=15.3), 7.31 (1H, dd, J=5.12, 3.65), 7.57–7.58 (1H, m), 7.69–7.73 (1H, m), 7.75–7.77 (1H, m).

ii) (E)-2-Thiophen-2-yl-ethenesulfonic acid amide (E)-2-Thiophen-2-yl-ethenesulfonic acid (1,1,3,3-tetramethyl-butyl)-amide (5.17 g, 17.2 mmol) was stirred for 15 minutes in a 1:1 mixture of trifluoroacetic acid and dichloromethane (40 mL). The mixture was concentrated in vacuo to afford a solid that was washed with dichloromethane (10 mL) in heptane (100 mL). The resultant solid was collected by suction filtration and dried under vacuum at ambient temperature to afford (E)-2-thiophen-2-yl-ethenesulfonic acid amide (2.89 g, 89%).

MS(ESI+): M=173(M-NH$_2$), 109 (M-SO$_2$NH$_2$).

$^1$H-NMR (400 MHz; d$^4$-MeOD): 7.08–7.12 (1H, d, J=15.5), 7.33–7.38 (1H, m), 7.60–7.62 (1H, m), 7.78–7.82 (2H, m).

iii) 4-Chloro-2-methoxy-benzoyl chloride

4-Chloro-2-methoxy-benzoic acid (0.50 g, 2.7 mmol) and DMF (50 μl) were added to dichloromethane (9 ml). Oxalyl chloride (0.47 ml, 5.4 mmol) was then added to the mixture and the resultant solution stirred at room temperature for 2 hours. The reaction was monitored to completion by LC-MS. The reaction was concentrated in vacuo to afford crude 4-chloro-2-methoxy-benzoyl chloride.

iv) (E)-2-Thiophen-2-yl-ethenesulfonic acid 4-chloro-2-methoxy-benzoylamide; sodium salt Sodium hydride (60% dispersion in mineral oil) (36 mg, 0.9 mmol) was added to a solution of (E)-2-thiophen-2-yl-ethenesulfonic acid amide (47 mg, 0.3 mmol) in dioxane (1 mL) and the mixture was shaken for 30 minutes. A solution of crude 4-chloro-2-methoxy-benzoyl chloride (63 μL, 0.45 mmol) in dioxane (0.5 mL) was added to the mixture and the whole was shaken at room temperature for 18 hours. Water (0.1 mL) was added to the mixture and the whole was concentrated in vacuo. The resultant residue was purified by preparative HPLC under neutral conditions to give (E)-2-thiophen-2-yl-ethenesulfonic acid 4-chloro-2-methoxy-benzoylamide sodium salt (15.7 mg, 14%).

MS(ESI+): M=358.0 (M+H)

$^1$H-NMR (400 MHz, d$^6$-DMSO): 7.35 (d, 1H, thiophene-5-H), 7.12 (m, 2H, phenyl-5-H, pheny-6-H), 7.08 (d, 1H, ethene), 6.82 (d, 1H, ethene, J=15.65 Hz, trans), 6.87 (m, 1H, thiophene-4-H), 6.74 (s, 1H, phenyl-3-H), 6.66 (d, 1H, thiophene-3-H), 3.51 (s, 3H, methoxy)

The following examples were prepared in an analogous manner as described for example 3-1 using the appropriate starting material:

| Example No. | Systematic Name | MS (M+H) | $^1$H-NMR |
|---|---|---|---|
| 3-2 | (E)-2-Thiophen-3-yl-ethenesulfonic acid 4-chloro-2-methyl-benzoylamide; sodium salt | 364.1(ESI+) | (400MHz, d$^6$-DMSO): 7.65(s, 1H, thiophene-2-H), 7.48(m, 2H, phenyl-5-H, ethene), 7.28(m, 1H, thiophene-5-H), 7.07(m, 4H, phenyl-3-H, phenyl-6-H, thiophene-4-H, ethene), 2.43(s, 3H, methyl) |
| 3-3 | (E)-2-Thiophen-2-yl-ethenesulfonic acid 4-chloro-2-methyl-benzoylamide; sodium salt | 364.1(ESI+) | (400MHz, d$^6$-DMSO): 7.59(m, 2H, thiophene, phenyl), 7.35(m, 1H, thiophene), 7.33(d, 1H, ethene, J=15.21Hz, trans), 7.18–7.06(m, 4H, phenyl, phenyl, thiophene, ethene), 2.42(s, 3H, methyl) |
| 3-4 | (E)-2-Thiophen-3-yl-ethenesulfonic acid 4-chloro-2-methoxy-benzoylamide; sodium salt | 358.0(ESI+) | (400MHz, d$^6$-DMSO): 7.51(m, 1H, thiophene-2-H), 7.34(m, 1H, thiophene-5-H), 7.14(m, 2H, phenyl-5-H, phenyl-6-H), 6.95(d, 1H, ethene), 6.89(d, 1H, ethene, J=15.65Hz, trans), 6.73(s, 1H, phenyl-3-H), 6.65(d, 1H, thiophene-4-H), 3.78(s, 3H, methoxy) |
| 3-5 | (E)-2-Thiophen-3-yl-ethenesulfonic acid 4-bromo-2-methyl-benzoylamide; sodium salt | 388.2(ESI+) | (400MHz, d$^6$-DMSO): 7.73(s, 1H, thiophene-2-H), 7.55(m, 1H, thiophene-5-H), 7.50(d, 1H, phenyl-5-H), 7.37(d, 1H, thiophene-4-H), 7.27(m, 2H, phenyl-3-H, phenyl-6-H), 7.16(m, 2H, ethene, ethene), 2.40(s, 3H, methyl) |
| 3-6 | (E)-2-Thiophen-2-yl-ethenesulfonic acid 4-bromo-2-methyl-benzoylamide; sodium salt | 388.2 | (400MHz, d$^6$-DMSO): 7.51(m, 1H, thiophene-5-H), 7.47(d, 1H, phenyl-5-H), 7.26(m, 4H, thiophene-4-H, phenyl-3-H, phenyl-6-H, ethene), 7.05(m, 2H, thiophene-3-H, ethene), 2.37(s, 3H, methyl) |
| 3-7 | (E)-2-Thiophen-3-yl-ethenesulfonic acid 2-bromo-4-methyl-benzoylamide; sodium salt | 388.2(ESI+) | (400MHz, d$^6$-DMSO): 7.85(m, 1H, thiophene-2-H), 7.67(m, 1H, phenyl-6-H), 7.49(m, 2H, phenyl-5-H, thiophene-5-H), 7.43(s, 1H, phenyl-3-H), 7.32(d, 1H, ethene), 7.24(d, 1H, ethene), J=15.7Hz, trans, 7.19(d, 1H, thiophene-4-H), 2.38(s, 3H, methyl) |
| 3-8 | (E)-2-Thiophen-2-yl- | 388.2(ESI+) | (400MHz, d$^6$-DMSO): 7.57(d, 1H, thiophene-5-H), 7.39(d, 1H, phenyl- |

| Example No. | Systematic Name | MS (M+H) | $^1$H-NMR |
|---|---|---|---|
| | ethenesulfonic acid 2-bromo-4-methyl-benzoylamide; sodium salt | | 5-H), 7.33(m, 3H, phenyl-3-H, thiophene-4-H, ethene), 7.07(m, 3H, thiophene-3-H, phenyl-6-H, ethene) |
| 3-9 | (E)-2-Thiophen-3-yl-ethenesulfonic acid 2-bromo-4-fluoro-benzoylamide; sodium salt | 392.2(ESI+) | (400MHz, d$^6$-DMSO): 7.63(m, 1H, thiophene-2-H), 7.43(m, 2H, phenyl-6-H, thiophene-5-H), 7.26(m, 2H, phenyl-3-H, thiophene-4-H), 7.08(d, 1H, ethene, J=15.3Hz, trans), 7.02(m, 2H, phenyl-5-H, ethene) |
| 3-10 | (E)-2-Thiophen-2-yl ethenesulfonic acid 2-bromo-4-fluoro-benzoylamide; sodium salt | 392.2(ESI+) | (400MHz, d$^6$-DMSO): 7.42(m, 2H, phenyl-6-H, thiophene-6-H), 7.26(m, 1H, phenyl-3-H), 7.20(m, 2H, thiophene-4-H, ethene), 6.92(d, 1H, ethene, J=15.3Hz, trans), 7.01(m, 1H, phenyl-5-H, 6.95(m, 1H, thiophene-3-H) |
| 3-11 | (E)-2-Thiophen-3-yl-ethenesulfonic acid 4-bromo-2-chloro-benzoylamide; sodium salt | 408.1(ESI+) | (400MHz, d$^6$-DMSO): 7.52(m, 1H, thiophene-2-H), 7.32(m, 2H, phenyl-3-H, thiophene-5-H), 7.21(bs, 2H, phenyl-5-H, phenyl-6-H), 7.15(d, 1H, thiophene-4-H), 6.97(d, 1H, ethene), 6.89(d, 1H, ethene), J=15.7Hz, trans |
| 3-12 | (E)-2-Thiophen-2-yl-ethenesulfonic acid 4-bromo-2-chloro-benzoylamide; sodium salt | 408.2(ESI+) | (400MHz, d$^6$-DMSO): 7.39(m, 2H, thiophene-5-H, phenyl-3-H), 7.26(bs, 2H, phenyl-5-H, phenyl-6-H), 7.15(m, 2H, thiophene-3-H, ethene), 6.86(d, 1H, ethene, J=15.65Hz, trans), 6.90(m, 1H, thiophene-4-H) |
| 3-13 | (E)-2-Thiophen-2-yl-ethenesulfonic acid 2,4-dimethyl-benzoylamide; sodium salt | 322.3(ESI+) | (400MHz, d$^6$-DMSO): 7.32(d, 1H, thiophene-5-H), 7.28(d, 1H, phenyl-6-H), 7.07(m, 2H, thiophene-3-H, ethene), 6.86(m, 2H, thiophene-4-H, ethene), 6.65(bs, 2H, phenyl-3-H, phenyl-5-H), 2.16(s, 3H, methyl), 2.00(s, 3H, methyl) |
| 3-14 | (E)-2-Thiophen-3-yl-ethenesulfonic acid 2,4-dimethyl-benzoylamide; sodium salt | 322.3(API+) | |

Example 4-1

(E)-2-Pyridin-3-yl-ethenesulfonic acid 4-chloro-2-methoxy-benzoylamide; sodium salt i) (E)-2-Pyridin-3-yl-ethenesulfonic acid (1,1,3,3-tetramethyl-butyl)-amide Methanesulfonyl chloride (2.1 mL, 27 mmol) in dichloromethane (10 mL) was added dropwise over 15 minutes to a solution of 2-hydroxy-2-pyridin-3-yl-ethanesulfonic acid (1,1,3,3-tetramethyl-butyl)-amide (5.67 g, 18 mmol) and triethylamine (15 mL, 108 mmol) in dichloromethane (40 mL) at 0° C. The mixture was warmed to ambient temperature and stirred for a further 1 hour. Water (50 mL) was added in one portion to the reaction mixture and the whole was extracted with dichloromethane (2×50 mL). The organic solution was dried over MgSO$_4$, filtered and concentrated in vacuo. The residue was purified by chromatography (SiO$_2$, ethyl acetate:heptane 1:1 to ethyl acetate) to afford (E)-2-pyridin-3-yl-ethenesulfonic acid (1,1,3,3-tetramethyl-butyl)-amide as a pale yellow solid (3.91 g, 73%).

MS(ESI+): M=297 (M+H)

$^1$H-NMR (400 MHz; CDCl$_3$) 0.87 (9H, s), 1.26 (6H, s), 1.45 (2H, s), 4.16 (1H, br s), 6.72 (1H, d, J=15.7), 7.16–7.19 (1H, m), 7.26 (1H, d, J=15.7), 7.59–7.62 (1H, m), 8.45–8.46 (1H, m), 8.54 (1H, m).

ii) (E)-2-Pyridin-3-yl-ethenesulfonic acid amide (E)-2-pyridin-3-yl-ethenesulfonic acid (1,1,3,3-tetramethyl-butyl)-amide (3.63 g, 12.3 mmol) was stirred for 3 hours in a 1:1 mixture of trifluoroacetic acid and dichloromethane (40 mL). The solvent was concentrated in vacuo to afford a yellow oil. The oil was dissolved in dichloromethane (50 mL) and washed with saturated sodium bicarbonate solution (50 mL), dried over MgSO$_4$, filtered and concentrated in vacuo to afford (E)-2-pyridin-3-yl-ethenesulfonic acid amide as a pale yellow solid (1.65 g, 73%).

MS(ESI+): M=185 (M+H)

¹H-NMR (400 MHz; d⁴-MeOD): 7.41 (1H, d, J=15.7), 7.55–7.61 (2H, m), 8.18–8.21 (1H, m), 8.64–8.66 (1H, m), 8.82–8.83 (1H, m).

iii) 4-Chloro-2-methoxy-benzoyl chloride

4-Chloro-2-methoxy-benzoic acid (0.50 g, 2.7 mmol) and DMF (50 μl) were added to dichloromethane (9 ml). Oxalyl chloride (0.47 ml, 5.4 mmol) was then added to the mixture and the resultant solution stirred at room temperature for 2 hours. The reaction was monitored to completion by LC-MS. The reaction was concentrated in vacuo to afford crude 4-chloro-2-methoxy-benzoyl chloride.

iv) (E)-2-Pyridin-3-yl-ethenesulfonic acid 4-chloro-2-methoxy-benzoylamide; sodium salt Sodium hydride (60% dispersion in mineral oil) (36 mg, 0.9 mmol) was added to a solution of (E)-2-pyridin-3-yl-ethenesulfonic acid amide (56 mg, 0.3 mmol) in dioxane (1 mL) and the mixture was shaken for 30 minutes. A solution of crude 4-chloro-2-methoxy-benzoyl chloride (63 μL, 0.45 mmol) in dioxane (0.5 mL) was added to the mixture and the whole was shaken at room temperature for 18 hours. Water (0.1 mL) was added to the mixture and the whole was concentrated in vacuo. The resultant residue was purified by preparative HPLC under neutral conditions to give (E)-2-pyridin-3-yl-ethenesulfonic acid 2-methoxy-4-chloro-benzoylamide sodium salt (37.2 mg, 33%).

MS(ESI+): M=353.3

¹H-NMR (400 MHz, d⁶-DMSO): 8.56 (m, 1H, pyridyl-2-H), 8.36 (m, 1H, pyridyl-6-H), 7.85 (m, 1H, pyridyl-4-H), 7.27 (d, 1H, ethene), 7.03 (d, 1H, ethene), J=15.25 Hz, trans, 7.25 (m, 1H, pyridyl-5-H), 7.21 (d, 1H, phenyl-6-H), 6.81 (s, 1H, phenyl-3-H), 6.73 (d, 1H, phenyl-5-H), 3.57 (s, 3H, methoxy)

The following examples were prepared in an analogous manner as described for example 4-1 using the appropriate starting material:

| Example No. | Systematic Name | MS (M+H) | ¹H-NMR |
|---|---|---|---|
| 4-2 | (E)-2-Pyridin-2-yl-ethenesulfonic acid 4-chloro-2-methyl-benzoylamide; sodium salt | 337.3(ESI+) | (400MHz, d⁶-DMSO): 8.50(m, 1H, pyridyl-6-H), 7.71(m, 1H, pyridyl-4-H), 7.60(d, 1H, ethene), 7.10(d, 1H, ethene, J=15.25Hz, trans), 7.52(d, 1H, phenyl-5-H), 7.49(d, 1H, pyridyl-3-H), 7.23(m, 1H, pyridyl-5-H), 7.05(m, 2H, phenyl-3-H, phenyl-6-H), 2.30(s, 3H, methyl) |
| 4-3 | (E)-2-Pyridin-2-yl-ethenesulfonic acid 4-chloro-2-methoxy-benzoylamide; sodium salt | 353.3(ESI+) | (400MHz, d⁶-DMSO): 8.44(m, 1H, pyridyl-6-H), 7.65(m, 1H, pyridyl-4-H), 7.49(d, 1H, ethene), 7.01(d, 1H, ethene, J=15.62Hz, trans), 7.41(d, 1H, phenyl-6-H), 7.18(m, 2H, pyridyl-3-H), pyridyl-5-H), 6.80(s, 1H, phenyl-3-H), 6.73(d, 1H, phenyl-5-H, 3.57(d, 3H, methoxy) |
| 4-4 | (E)-2-Pyridin-2-yl-ethenesulfonic acid 4-bromo-2-methyl-benzoylamide; sodium salt | 383.2(ESI+) | (400MHz, d⁶-DMSO): 8.39(m, 1H, pyridyl-6-H), 7.59(m, 1H, pyridyl-4-H), 7.48(d, 1H, ethene), 6.98(d, 1H, ethene, J=15.30Hz, trans), 7.37(d, 1H, phenyl-3-H), 7.33(m, 1H, phenyl-5-H), 7.11(m, 1H, pyridyl-5-H), 7.09(d, 1H, phenyl-3-H), 7.06(d, 1H, phenyl-6-H), 2.21(s, 3H, methyl) |
| 4-5 | (E)-2-Pyridin-2-yl-ethenesulfonic acid 2-bromo-4-methyl-benzoylamide; sodium salt | 383.2(ESI+) | (400MHz, d⁶-DMSO): 8.42(m, 1H, pyridyl-6-H), 7.64(m, 1H, pyridyl-4-H), 7.50(d, 1H, ethene), 7.03(d, 1H, ethene, J=15.30Hz, trans), 7.41(d, 1H, phenyl-5-H), 7.23(d, 1H, phenyl-5-H), 7.15(m, 2H, pyridyl-5-H, phenyl-3-H), 6.92(d, 1H, phenyl-6-H), 2.10(s, 3H, methyl) |
| 4-6 | (E)-2-Pyridin-2-yl-ethenesulfonic acid 2-bromo-4-fluoro-benzoylamide; sodium salt | 387.2(ESI+) | (400MHz, d⁶-DMSO): 8.60(m, 1H, pyridyl-6-H), 7.81(m, 1H, pyridyl-4-H), 7.70(d, 1H, ethene), 7.21(d, 1H, ethene, J=15.65Hz, trans), 7.58(m, 2H, pyridyl-3-H, phenyl-3-H), 7.41(m, 1H, phenyl-5-H), 7.33(m, 1H, phenyl-6-H), 7.15(m 1H, pyridyl-5-H) |
| 4-7 | (E)-2-Pyridin-2-yl-ethenesulfonic acid 4-bromo-2-chloro-benzoylamide; sodium salt | 403.2(ESI+) | (400MHz, d⁶-DMSO): 8.53(m, 1H, pyridyl-6-H), 7.74(m, 1H, pyridyl-4-H), 7.58(d, 1H, ethene), 7.13(d, 1H, ethene, J=15.30Hz, trans), 7.51(m, 2H, pyridyl-3-H, phenyl-2-H), 7.39(s, 2H, phenyl-5- |

-continued

| Example No. | Systematic Name | MS (M+H) | ¹H-NMR |
|---|---|---|---|
| | | | H, phenyl-6-H), 7.27(m, 1H, pyridyl-5-H) |
| 4-8 | (E)-2-Pyridin-3-yl-ethenesulfonic acid 4-chloro-2-methyl-benzoylamide; sodium salt | 337.3(ESI+) | (400MHz, D⁶-DMSO): 8.67(s, 1H, pyridyl-2-H), 8.47(m, 1H, pyridyl-6-H), 7.96(m, 1H, pyridyl-4-H), 7.55(d, 1H, phenyl-6-H), 7.55(d, 1H, ethene), 7.16(d, 1H, ethene, J=15.62Hz, trans), 7.36(m, 1H, pyridyl-5-H), 7.09(m, 2H, phenyl-3-H, phenyl-5-H), 2.37(s, 3H, methyl) |
| 4-9 | (E)-2-Pyridin-3-yl-ethenesulfonic acid 4-bromo-2-methyl-benzoylamide; sodium salt | 383.2(ESI+) | (400MHz, D⁶-DMSO): 8.52(s, 1H, pyridyl-2-H), 8.33(m, 1H, pyridyl-6-H), 7.82(m, 1H, pyridyl-4-H), 7.34(d, 1H, phenyl-5-H), 7.27(d, 1H, ethene), 7.02(d, 1H, ethene, J=16.25Hz, trans), 7.21(m, 1H, pyridyl-5-H), 7.11(s, 1H, phenyl-3-H), 7.08(m, 1H, phenyl-6-H), 2.23(s, 3H, methyl) |
| 4-10 | (E)-2-Pyridin-3-yl-ethenesulfonic acid 2-bromo-4-methyl-benzoylamide; sodium salt | 383.2(ESI+) | (400MHz, D⁶-DMSO): 8.58(s, 1H, pyridyl-2-H), 8.39(m, 1H, pyridyl-6-H), 7.87(m, 1H, pyridyl-4-H), 7.28(m, 2H, phenyl-5-H), pyridyl-5-H), 7.27(d, 1H, ethene, 7.08(d, 1H, ethane, J=16.37Hz, trans), 7.18(s, 1H, phenyl-3-H), 6.95(d, 1H, phenyl-6-H), 2.10(s, 3H, methyl) |
| 4-11 | (E)-2-Pyridin-3-yl-ethenesulfonic acid 4-bromo-2-chloro-benzoylamide; sodium salt | 403.2(ESI+) | (400MHz, d⁶-DMSO): 8.72(m, 1H, pyridyl-2-H), 8.52(m, 1H, pyridyl-6-H), 8.02(d, 1H, pyridyl-4-H), 7.57(s, 1H, phenyl-3-H), 7.59(m, 2H, phenyl-5-H, phenyl-6-H), 7.43(d, 1H, ethene), 7.23(d, 1H, ethene, J=16.00Hz, trans), 7.42(m, 1H, pyridyl-5-H) |
| 4-12 | (E)-2-(6-Methoxy-pyridin-3-yl)-ethenesulfonic acid 4-chloro-2-methyl-benzoylamide; sodium salt | 367.2(ESI+) | (400MHz, d⁶-DMSO): 8.13(m, 1H, pyridyl-2-H), 7.78(m, 1H, pyridyl-4-H), 7.41(d, 1H, phenyl-6-H), 7.12(d, 1H, ethene), 6.98(d, 1H, ethene, J=15.25Hz, trans), 6.96(m, 2H, phenyl-3-H, phenyl-5-H), 6.66(m, 1H, pyridyl-5-H), 3.70(s, 3H, methoxy), 2.24(s, 3H, methyl) |
| 4-13 | (E)-2-(6-Methoxy-pyridin-3-yl)-ethenesulfonic acid 2-bromo-4-fluoro-benzoylamide; sodium salt | 417.2(ESI+) | (400MHz, d⁶-DMSO): 8.36(m, 1H, phenyl-3-H), 8.01(m, 1H, phenyl-5-H), 7.59(m, 1H, pyridyl-4-H), 7.45(m, 1H, phenyl-6-H), 7.31(d, 1H, ethene), 7.22(d, 1H, ethene, J=15.62Hz, trans), 7.19(m, 1H, pyridyl-3-H), 6.89(m, 1H, pyridyl-5-H), 3.93(s, 3H, methoxy) |
| 4-14 | (E)-2-(6-Methyl-pyridin-2-yl)-ethenesulfonic acid 4-chloro-2-methyl-benzoylamide; sodium salt | 351.3(ESI+) | (400MHz, d⁶-DMSO): 7.56(m, 1H, pyridyl-4-H), 7.53(d, 1H, ethene), 7.03(d, 1H, ethene, J=15.70Hz, trans), 7.49(d, 1H, phenyl-5-H), 7.24(d, 1H, pyridyl-3-H), 7.07(d, 1H, pyridyl-5-H), 7.02(m, 2H, phenyl-3-H, phenyl-6-H), 2.39(s, 3H, methyl), 2.30(s, 3H, methyl) |
| 4-15 | (E)-2-(6-Methyl-pyridin-2-yl)-ethenesulfonic acid 2-bromo-4-fluoro-benzoylamide; sodium salt | 401.2(ESI+) | (400 MHz, d⁶-DMSO): 7.44(m, 1H, pyridyl-4-H), 7.38(d, 1H, ethene), 6.92(d, 1H, ethene, J=15.25Hz, trans), 7.32(m, 1H, pyridyl-3-H), 7.16(m, 1H, phenyl-5-H), 7.12(d, 1H, phenyl-6-H), 6.95(m, 1H, phenyl-3-H), 6.92(m, 1H, pyridyl-3-H), 1.78(s, 3H, methyl) |

-continued

| Example No. | Systematic Name | MS (M+H) | ¹H-NMR |
|---|---|---|---|
| 4-16 | (E)-2-Pyridin-3-yl-ethenesulfonic acid 2,4-dimethyl-benzoylamide; sodium salt | 317.3(ESI+) | (400MHz, d⁶-DMSO): 8.71(s, 1H, pyridyl-2-H), 8.52(m, 1H, pyridyl-6-H), 8.01(m, 1H, pyridyl-4-H), 7.53(m, 1H, phenyl-5-H), 7.48(m, 1H, ethene), 7.19(d, 1H, ethene, J=16.00Hz, trans), 7.40(m, 1H, pyridyl-5-H), 6.88(m, 2H, phenyl-3-H, phenyl-6-H), 2.41(s, 3H, methyl), 2.24(s, 3H, methyl) |
| 4-17 | (E)-2-Pyridin-4-yl-ethenesulfonic acid 2,4-dimethyl-benzoylamide; sodium salt | 317.3(API+) | (400MHz, d⁶-DMSO): 2.03(s, 3H); 2.19(s, 3H); 6.65–6.75(m, 2H); 6.91(d, 15.7Hz, 1H); 7.29–7.35(m, 3H); 7.37(d, 15.7Hz, 1H); 8.35(d, 4.6Hz, 2H) |
| 4-18 | (E)-2-Benzo[b]thiophen-3-yl-ethenesulfonic acid 4-chloro-2-methyl-benzoylamide; sodium salt | 392.9(ESI+) | (400MHz, d⁶-DMSO): 8.16(s, 1H), 8.09(d, J=7.6Hz, 1H), 8.05(d, J=7.7Hz, 1H), 7.64(d, J=7.7Hz, 1H), 7.56–7.46(m, 4H), 7.20–7.17(m, 2H), 2.46(s, 3H) |
| 4-19 | (E)-2-Benzo[b]thiophen-3-yl-ethenesulfonic acid 2-bromo-4-fluoro-benzoylamide; sodium salt | 441.5(ESI+) | (400MHz, d⁶-DMSO): 8.17(s, 1H), 8.09(d, J=8.3Hz, 1H), 8.06(d, J=8.3Hz, 1H), 7.60(t, J=7.5Hz, 1H), 7.55–7.43(m, 5H), 7.19(t, J=7.3Hz, 1H) |

Example 5-1

(E)-2-Thiophen-2-yl-ethenesulfonic acid 4-fluoro-2-methyl-benzoylamide

To a solution of 4-fluoro-2-methyl-benzoic acid (197 mg, 1.27 mmol) and (E)-2-thiophen-2-yl-ethenesulfonic acid amide (155 mg, 0.82 mmol) (which was prepared analogously to example 1-1 steps i) to ii) starting from 2-bromo-thiophene) in dichloromethane (5 mL) and N,N-dimethylformamide (DMF) (2 mL) is added 1-ethyl-3-(3'-dimethylaminopropyl)carbodiimide (EDCI) (277 mg, 1.45 mmol) and 4-(dimethylamino)-pyridine (DMAP) (172 mg, 1.41 mmol) at room temperature (RT). The mixture was stirred at RT for 24 h, and solvent removed under reduced pressure. The crude reaction mixture is partitioned between aq. 1M HCl (25 mL) and ethyl acetate (25 mL). The organic phase is separated and washed with aq. 1M HCl (2×25 mL), and then with sat. aq. K₂CO₃ solution (3×25 mL) and dried (sodium sulfate) and concentrated in vacuo. After flash chromatography (heptane/ethyl acetate 3:1 to 1:1) ((E)-2-Thiophen-2-yl-ethenesulfonic acid 4-fluoro-2-methyl-benzoylamide can be isolated as a white solid. Yield 65 mg (15%)

MS: M=326.1 (ESI+)

¹H-NMR (400 MHz, CDCl₃): d=8.24 (br. s, 1H), 7.91 (d, J=15.2 Hz, 1H), 7.54–7.49 (m, 2H), 7.40 (d, J=3.5 Hz, 1H), 7.12 (dd, J=4.8, 3.5 Hz, 1H), 7.00–6.93 (m, 2H), 6.92 (d, J=15.2 Hz, 1H), 2.51 (s, 3H).

What is claimed is:

1. Compounds of formula I:

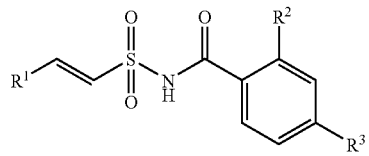

formula I wherein:

R¹ is a mono- or bicyclic heteroaryl which is optionally substituted one to three times by alkyl, or one or two times by halogen, cyano, alkoxy, halogenated alkyl, halogenated alkoxy or amino;

R² is selected from the group consisting of chlorine, bromine, methyl, trifluoromethyl and methoxy;

R³ is selected from the group consisting of chlorine, bromine, fluorine, methyl and trifluoromethyl;

or pharmaceutically acceptable salts thereof.

2. The compounds of claim 1, wherein R² and R³ are both chlorine.

3. The compounds of claim 1, wherein R¹ is a monocyclic heteroaryl which is optionally substituted one or two times by alkyl, halogen, alkoxy or halogenated alkyl.

4. The compounds of claim 1, wherein R¹ is a thienyl or pyridyl which is optionally substituted one or two times by alkyl, halogen, alkoxy or halogenated alkyl.

5. The compounds of claim 1, wherein R¹ is a mono- or bicyclic heteroaryl which is optionally substituted one to three times by alkyl, or one or two times by halogen, alkoxy or halogenated alkyl.

6. The compounds of claim 4, wherein $R^1$ is a thienyl or pyridyl which is optionally substituted one or two times by alkyl or alkoxy.

7. The compounds of claim 6, wherein $R^1$ is a thienyl.

8. The compounds of claim 6, wherein $R^1$ is a pyridyl which is optionally substituted one or two times by alkyl or alkoxy.

9. The compounds of claim 3, wherein $R^1$ is thienyl or isoxazolyl which is optionally substituted one or two times by alkyl.

10. A compound of claim 1, selected from the group consisting of:
    (E)-2-Thiophen-2-yl-ethenesulfonic acid 2,4-dichloro-benzoylamide;
    (E)-2-Thiophen-3-yl-ethenesulfonic acid 2,4-dichloro-benzoylamide;
    (E)-2-(3-Methyl-thiophen-2-yl)-ethenesulfonic acid 2,4-dichloro-benzoylamide;
    (E)-2-(5-Methyl-thiophen-2-yl)-ethenesulfonic acid 2,4-dichloro-benzoylamide;
    (E)-2-(4-Methyl-thiophen-2-yl)-ethenesulfonic acid 2,4-dichloro-benzoylamide; and
    (E)-2-(3,5-Dimethyl-isoxazol-4-yl)-ethenesulfonic acid 2,4-dichloro-benzoylamide; sodium salt.

11. The compounds of claim 3, wherein $R^1$ is pyridyl which is optionally substituted one or two times by alkyl or alkoxy.

12. A compound of claim 1, selected from the group consisting of:
    (E)-2-Pyridin-2-yl-ethenesulfonic acid 2,4-dichloro-benzoylamide; sodium salt;
    (E)-2-Pyridin-3-yl-ethenesulfonic acid 2,4-dichloro-benzoylamide; sodium salt;
    (E)-2-Pyridin-4-yl-ethenesulfonic acid 2,4-dichloro-benzoylamide; sodium salt;
    (E)-2-(6-Methoxy-pyridin-3-yl)-ethenesulfonic acid 2,4-dichloro-benzoylamide; sodium salt; and
    (E)-2-(6-Methyl-pyridin-2-yl-ethenesulfonic acid 2,4-dichloro-benzoylamide; sodium salt.

13. The compounds of claim 3, wherein $R^1$ is thienyl or pyridyl which is optionally substituted one or two times by halogen or halogenated alkyl.

14. A compound of claim 1, selected from the group consisting of:
    (E)-2-(4-Bromo-thiophen-2-yl)-ethenesulfonic acid 2,4-dichloro-benzoylamide; sodium salt;
    (E)-2-(3-Bromo-thiophen-2-yl)-ethenesulfonic acid 2,4-dichloro-benzoylamide; sodium salt;
    (E)-2-(6-Trifluoromethyl-pyridin-3-yl)-ethenesulfonic acid 2,4-dichloro-benzoylamide; sodium salt;
    (E)-2-(6-Chloro-pyridin-3-yl)-ethenesulfonic acid 2,4-dichloro-benzoylamide; sodium salt; and
    (E)-2-(2-Chloro-pyridin-3-yl)-ethenesulfonic acid 2,4-dichloro-benzoylamide; sodium salt.

15. The compounds of claim 3, wherein $R^1$ is pyrimidyl or thiazolyl.

16. A compound of claim 1, selected from the group consisting of:
    (E)-2-Pyrimidin-5-yl-ethenesulfonic acid 2,4-dichloro-benzoylamide; sodium salt; and
    (E)-2-Thiazol-2-yl-ethenesulfonic acid 2,4-dichloro-benzoylamide; sodium salt.

17. The compounds of claim 3, wherein $R^1$ is benzothiophenyl.

18. A compound of claim 1, selected from the group consisting of:
    (E)-2-Benzo[b]thiophen-3-yl-ethenesulfonic acid 2-chloro-4-fluoro-benzoylamide; sodium salt;
    (E)-2-Benzo[b]thiophen-3-yl-ethenesulfonic acid 2,4-dichloro-benzoylamide; sodium salt;
    (E)-2-Benzo[b]thiophen-3-yl-ethenesulfonic acid 4-fluoro-2-trifluoromethyl-benzoylamide; sodium salt;
    (E)-2-Benzo[b]thiophen-3-yl-ethenesulfonic acid 2,4-ditrifluoromethyl-benzoylamide; sodium salt;
    (E)-2-Benzo[b]thiophen-3-yl-ethenesulfonic acid 4-chloro-2-methyl-benzoylamide; sodium salt; and
    (E)-2-Benzo[b]thiophen-3-yl-ethenesulfonic acid 2-bromo-4-fluoro-benzoylamide; sodium salt.

19. The compounds of claim 1, wherein $R^2$ is chlorine and $R^3$ is bromine.

20. A compound of claim 1, selected from the group consisting of:
    (E)-2-Pyridin-2-yl-ethenesulfonic acid 4-bromo-2-chloro-benzoylamide; sodium salt;
    (E)-2-Pyridin-3-yl-ethenesulfonic acid 4-bromo-2-chloro-benzoylamide; sodium salt;
    (E)-2-Thiophen-3-yl-ethenesulfonic acid 4-bromo-2-chloro-benzoylamide; sodium salt; and
    (E)-2-Thiophen-2-yl-ethenesulfonic acid 4-bromo-2-chloro-benzoylamide; sodium salt.

21. The compounds of claim 1, wherein $R^2$ is chlorine and $R^3$ is fluorine.

22. A compound of claim 1, selected from the group consisting of:
    (E)-2-Pyridin-2-yl-ethenesulfonic acid 2-chloro-4-fluoro-benzoylamide; sodium salt;
    (E)-2-Pyridin-3-yl-ethenesulfonic acid 2-chloro-4-fluoro-benzoylamide; sodium salt;
    (E)-2-(6-Methoxy-pyridin-3-yl)-ethenesulfonic acid 2-chloro-4-fluoro-benzoylamide; sodium salt;
    (E)-2-Thiophen-3-yl-ethenesulfonic acid 2-chloro-4-fluoro-benzoylamide; sodium salt;
    (E)-2-Thiophen-2-yl-ethenesulfonic acid 2-chloro-4-fluoro-benzoylamide; sodium salt; and
    (E)-2-(6-Methyl-pyridin-2-yl)-ethenesulfonic acid 2-chloro-4-fluoro-benzoylamide; sodium salt.

23. The compounds of claim 1, wherein $R^2$ is bromine and $R^3$ is fluorine.

24. A compound of claim 1, selected from the group consisting of:
    (E)-2-Pyridin-2-yl-ethenesulfonic acid 2-bromo-4-fluoro-benzoylamide; sodium salt;
    (E)-2-(6-Methoxy-pyridin-3-yl)-ethenesulfonic acid 2-bromo-4-fluoro-benzoylamide; sodium salt;
    (E)-2-(6-Methyl-pyridin-2-yl)-ethenesulfonic acid 2-bromo-4-fluoro-benzoylamide; sodium salt;
    (E)-2-Thiophen-3-yl-ethenesulfonic acid 2-bromo-4-fluoro-benzoylamide; sodium salt; and
    (E)-2-Thiophen-2-yl-ethenesulfonic acid 2-bromo-4-fluoro-benzoylamide; sodium salt.

25. The compounds of claim 1, wherein $R^2$ is bromine and $R^3$ is methyl.

26. A compound of claim 1, selected from the group consisting of:
    (E)-2-Pyridin-2-yl-ethenesulfonic acid 2-bromo-4-methyl-benzoylamide; sodium salt;
    (E)-2-Pyridin-3-yl-ethenesulfonic acid 2-bromo-4-methyl-benzoylamide; sodium salt;
    (E)-2-Thiophen-3-yl-ethenesulfonic acid 2-bromo-4-methyl-benzoylamide; sodium salt; and
    (E)-2-Thiophen-2-yl-ethenesulfonic acid 2-bromo-4-methyl-benzoylamide; sodium salt.

27. The compounds of claim 1, wherein $R^2$ is methyl and $R^3$ is chlorine.

28. A compound of claim 1, selected from the group consisting of:
- (E)-2-Pyridin-2-yl-ethenesulfonic acid 4-chloro-2-methyl-benzoylamide; sodium salt;
- (E)-2-Pyridin-3-yl-ethenesulfonic acid 4-chloro-2-methyl-benzoylamide; sodium salt;
- (E)-2-(6-Methoxy-pyridin-3-yl)-ethenesulfonic acid 4-chloro-2-methyl-benzoylamide; sodium salt;
- (E)-2-(6-Methyl-pyridin-2-yl)-ethenesulfonic acid 4-chloro-2-methyl-benzoylamide; sodium salt;
- (E)-2-Thiophen-3-yl-ethenesulfonic acid 4-chloro-2-methyl-benzoylamide; sodium salt; and
- (E)-2-Thiophen-2-yl-ethenesulfonic acid 4-chloro-2-methyl-benzoylamide; sodium salt.

29. The compounds of claim 1, wherein $R^2$ is methyl and $R^3$ is bromine.

30. A compound of claim 1, selected from the group consisting of:
- (E)-2-Pyridin-2-yl-ethenesulfonic acid 4-bromo-2-methyl-benzoylamide; sodium salt;
- (E)-2-Pyridin-3-yl-ethenesulfonic acid 4-bromo-2-methyl-benzoylamide; sodium salt;
- (E)-2-Thiophen-3-yl-ethenesulfonic acid 4-bromo-2-methyl-benzoylamide; sodium salt; and
- (E)-2-Thiophen-2-yl-ethenesulfonic acid 4-bromo-2-methyl-benzoylamide; sodium salt.

31. The compounds of claim 1, wherein $R^2$ is methyl and $R^3$ is fluorine.

32. A compound of claim 1, wherein the compound is:
- (E)-2-Thiophen-2-yl-ethenesulfonic acid 4-fluoro-2-methyl-benzoylamide.

33. The compounds of claim 1, wherein $R^2$ is methyl and $R^3$ is methyl.

34. A compound of claim 1, selected from the group consisting of:
- (E)-2-Thiophen-2-yl-ethenesulfonic acid 2,4-dimethyl-benzoylamide; sodium salt;
- (E)-2-Pyridin-3-yl-ethenesulfonic acid 2,4-dimethyl-benzoylamide; sodium salt;
- (E)-2-Thiophen-3-yl-ethenesulfonic acid 2,4-dimethyl-benzoylamide; sodium salt; and
- (E)-2-Pyridin-4-yl-ethenesulfonic acid 2,4-dimethyl-benzoylamide; sodium salt.

35. The compounds of claim 1, wherein $R^2$ is trifluoromethyl and $R^3$ is fluorine.

36. A compound of claim 1, selected from the group consisting of:
- (E)-2-Pyridin-2-yl-ethenesulfonic acid 4-fluoro-2-trifluoromethyl-benzoylamide; sodium salt;
- (E)-2-Pyridin-3-yl-ethenesulfonic acid 4-fluoro-2-trifluoromethyl-benzoylamide; sodium salt;
- (E)-2-(6-Methoxy-pyridin-3-yl)-ethenesulfonic acid 4-fluoro-2-trifluoromethyl-benzoylamide; sodium salt;
- (E)-2-(6-Methyl-pyridin-2-yl)-ethenesulfonic acid 4-fluoro-2-trifluoromethyl-benzoylamide; sodium salt; and
- (E)-2-Thiophen-3-yl-ethenesulfonic acid 4-fluoro-2-trifluoromethyl-benzoylamide; sodium salt.

37. The compounds of claim 1, wherein $R^2$ is trifluoromethyl and $R^3$ is trifluoromethyl.

38. A compound of claim 1, selected from the group consisting of:
- (E)-2-Pyridin-2-yl-ethenesulfonic acid 2,4-bis-trifluoromethyl-benzoylamide; sodium salt;
- (E)-2-Pyridin-3-yl-ethenesulfonic acid 2,4-bis-trifluoromethyl-benzoylamide; sodium salt;
- (E)-2-(6-Methoxy-pyridin-3-yl)-ethenesulfonic acid 2,4-bis-trifluoromethyl-benzoylamide; sodium salt;
- (E)-2-(6-Methyl-pyridin-2-yl)-ethenesulfonic acid 2,4-bis-trifluoromethyl-benzoylamide; sodium salt;
- (E)-2-Thiophen-3-yl-ethenesulfonic acid 2,4-bis-trifluoromethyl-benzoylamide; sodium salt;
- (E)-2-Thiophen-2-yl-ethenesulfonic acid 2,4-bis-trifluoromethyl-benzoylamide; sodium salt; and
- (E)-2-Pyridin-3-yl-ethenesulfonic acid 2,4-bis-trifluoromethyl-benzoylamide.

39. The compounds of claim 1, wherein $R^2$ is methoxy and $R^3$ is chlorine.

40. A compound of claim 1, selected from the group consisting of:
- (E)-2-Pyridin-3-yl-ethenesulfonic acid 4-chloro-2-methoxy-benzoylamide; sodium salt;
- (E)-2-Pyridin-2-yl-ethenesulfonic acid 4-chloro-2-methoxy-benzoylamide; sodium salt;
- (E)-2-Thiophen-2-yl-ethenesulfonic acid 4-chloro-2-methoxy-benzoylamide; sodium salt; and
- (E)-2-Thiophen-3-yl-ethenesulfonic acid 4-chloro-2-methoxy-benzoylamide; sodium salt.

41. The compounds of claim 1, wherein $R^3$ is fluorine.

42. The compounds of claim 1, wherein:
$R^1$ is thienyl;
$R^2$ is chlorine, bromine or trifluoromethyl; and
$R^3$ is fluorine.

43. The compounds of claim 1, wherein $R^3$ is chlorine.

44. The compounds of claim 1, wherein:
$R^1$ is pyridyl which is optionally substituted one or two times by alkyl, halogen, alkoxy or halogenated alkyl;
$R^2$ is methyl or methoxy; and
$R^3$ is chlorine.

45. A process for the preparation of the compounds of formula I of claim 1, comprising the steps of
a) reacting a compound of formula II

formula II wherein $R^1$ has the significance given for formula I in claim 1 and X is iodine or bromine, with ethenesulfonic acid (1,1,3,3-tetramethyl-butyl)-amide,

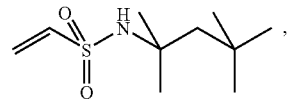

to give the compounds of formula III,

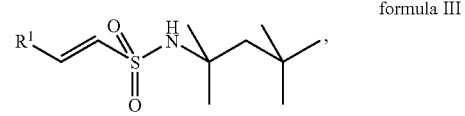

formula III wherein $R^1$ has the significance given for formula I in claim 1, b) cleaving the 1,1,3,3-tetramethyl-butyl group of the compounds of formula III to give the free sulfonamides of formula IV,

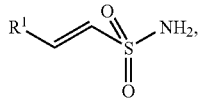

formula IV wherein R¹ has the significance given for formula I, and
c) reacting the sulfonamides of formula IV with the benzoic acid of formula IX,

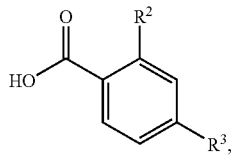

formula IX which is activated before, and wherein R² and R³ have the significance given for formula I in claim 1,
to give the compounds of formula I,

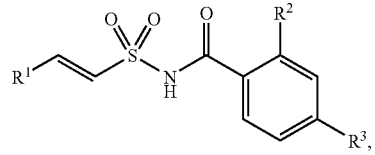

formula I wherein R¹, R² and R³ have the significance given for formula I in claim 1.

46. A process for the preparation of the compounds of formula I of claim 1, comprising the steps of
a) reacting a compound of formula V

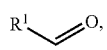

formula V wherein R¹ has the significance given for formula I,
with N-(1,1,3,3-tetramethyl-butyl)-methanesulfonamide,

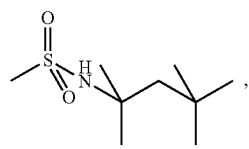

to give the compounds of formula VI,

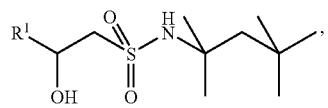

formula VI wherein R¹ has the significance given for formula I in claim 1,
b) dehydrate the compounds of formula VI to give the compounds of formula III,

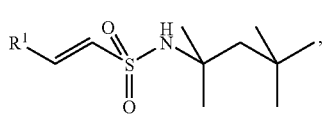

formula III wherein R¹ has the significance given for formula I in claim 1,
c) cleaving the 1,1,3,3-tetramethyl-butyl group of the compounds of formula III to give the free sulfonamides of formula IV,

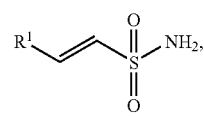

formula IV wherein R¹ has the significance given for formula I in claim 1,
d) reacting the sulfonamides of formula IV with the benzoic acid of formula IX,

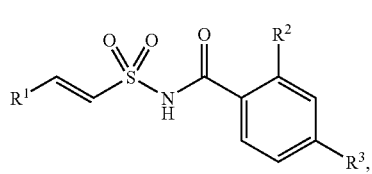

formula IX which is activated before, and wherein R² and R³ have the significance given for formula I in claim 1,
to give the compounds of formula I,

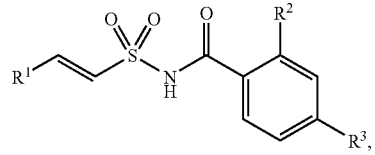

formula I wherein R¹, R² and R³ have the significance given for formula I in claim 1.

47. A process for the preparation of the compounds of formula I of claim 1, comprising reacting a compound of formula IV,

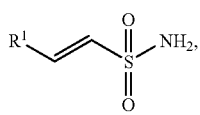

wherein R¹ has the significance given for formula I in claim 1;
with the benzoic acid of formula IX,

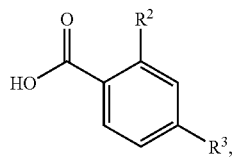

which is activated before, and wherein R² and R³ have the significance given for formula I in claim 1,
to give the compounds of formula I,

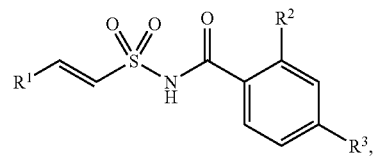

wherein R¹, R² and R³ have the significance given for formula I in claim 1.

48. A pharmaceutical composition comprising a compound of claim 1 together with pharmaceutically acceptable adjuvants.

* * * * *